United States Patent
Damaghi et al.

(10) Patent No.: US 6,306,121 B1
(45) Date of Patent: Oct. 23, 2001

(54) DISPOSABLE ELASTIC ABSORBENT ARTICLE HAVING TRIPLE MEMBER CLOSURE

(75) Inventors: Kambiz Damaghi, Kings Point, NY (US); Mordechai Turi, Mill Hall, PA (US); Michael Kauschke, Yonkers, NY (US)

(73) Assignee: First Quality Enterprises, Inc., McElhattan, PA (US)

( * ) Notice: Subject to any disclaimer, the term of this patent is extended or adjusted under 35 U.S.C. 154(b) by 0 days.

(21) Appl. No.: 09/149,265

(22) Filed: Sep. 8, 1998

Related U.S. Application Data

(63) Continuation-in-part of application No. 09/097,198, filed on Jun. 12, 1998.
(51) Int. Cl.⁷ .............................. A61F 13/15; A61F 13/20
(52) U.S. Cl. ................. 604/385.03; 604/385.01; 604/385.27; 604/387
(58) Field of Search .................. 604/385.01, 385.27, 604/392, 396, 393, 394, 385.03, 385.23, 385.25, 385.3, 391, 358, 387; D2/625; D24/125, 126

(56) References Cited

U.S. PATENT DOCUMENTS

| | | | | |
|---|---|---|---|---|
| 2,493,113 | * | 1/1950 | Dance | 128/287 |
| 5,411,498 | * | 5/1995 | Fahrenkrug et al. | 604/385.2 |

* cited by examiner

Primary Examiner—John G. Weiss
Assistant Examiner—Michele Kidwell

(57) ABSTRACT

An absorbent article is provided which comprises an absorbent body having a front waist portion, a back waist portion, a crotch portion, a pair of spaced apart leg openings, and a fastening region intermediate the crotch portion and the front waist portion. An elasticized band member is attached to the back waist portion and has a left hand band portion and a right hand band portion, both extending angularly from the area of the back waist portion toward the fastening region. The ends of each of the band portions are adapted to be engaged to one another and to the fastening region, and they may be tensioned to securely fasten the absorbent article to the body of the wearer.

14 Claims, 24 Drawing Sheets

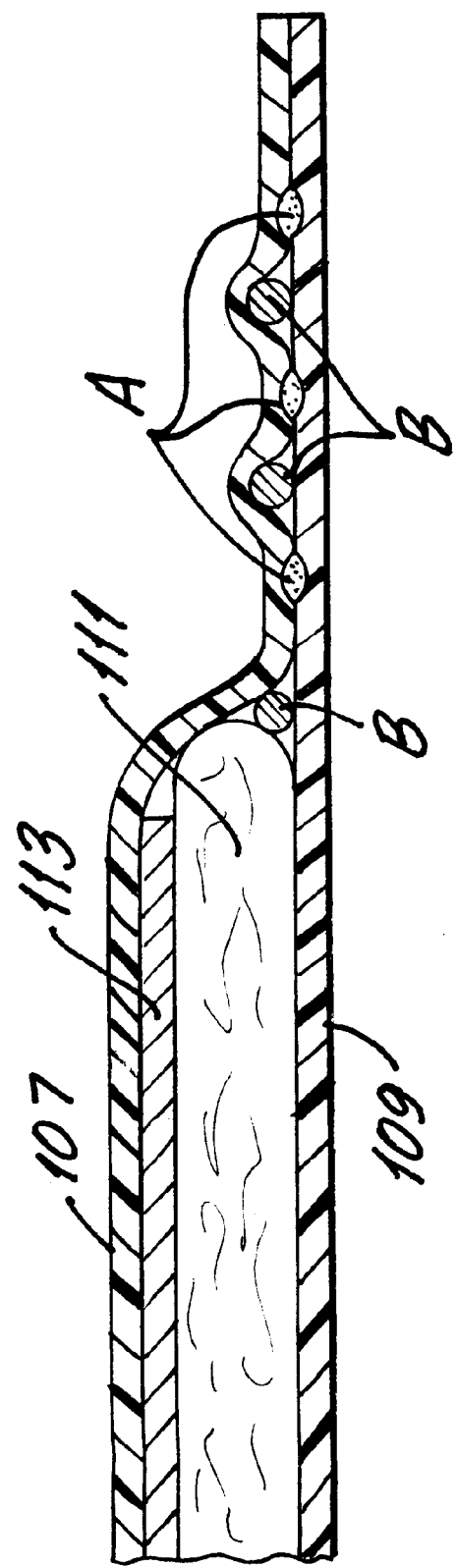

DISPOSABLE ELASTIC ABSORBENT ARTICLE HAVING TRIPLE MEMBER CLOSURE

RELATED APPLICATION

This application is a continuation-in-part of pending application Ser. No. 09/097,198 filed Jun. 12, 1998.

FIELD OF THE INVENTION

The present invention relates generally to absorbent articles such as disposable diapers, and is more particularly related to infant training pants and adult incontinent underpants, briefs and guards used for absorption and containment of urine and other body exudates. More particularly, the present invention relates to such adult incontinent articles which are easy to wear, securely fit against the body contours for effective prevention against leakage of urine and other body exudates, and which are also easy to remove. In one particular aspect, this invention relates to adults incontinent underpants, briefs and guards having elastically contractible waistbands and triple member closure for improved body fit and enhanced prevention of leakage of urine and other body exudates.

BACKGROUND OF THE INVENTION

Disposable absorbent articles such as disposable baby diapers and adult incontinent briefs, underpants, guards and the like articles are widely used in homes and various health care facilities and institutions. Indeed the use of such articles has become a common sanitary practice, and while initially such absorbent articles were used mostly for baby care, more recently their use has been expanded for adults as well. In both instances, the absorbent article must be designed to effectively prevent leakage of urine and other fecal materials, while insuring body fit and comfort.

Present commercially available absorbent articles are generally unitary in structure, pre-shaped and pre-folded, and comprise an absorptive pad having a liquid permeable top sheet facing the wearer's body, a liquid impermeable backsheet on the opposite side, and an absorbent sheet or panel disposed between the top sheet and the back sheet. The absorbent article comprises a front side portion, a crotch portion and a backside portion, and further includes elastic members along the circumference of the waist and around the leg openings. While the heretofore commercially available absorbent articles have been somewhat effective against leakage of body fluids and fecal materials, and have therefore met some degree of acceptability, they have not been entirely satisfactory for their intended applications. In other words, they have not proven to be entirely leak proof, nor have they completely prevented issuance of the body exudates outside the diaper or the underpants. These deficiencies are primarily due to inadequate and loose body fit, which result in leakage of the body fluids and solids through the legs' openings. These problems are even more pronounced in case of adults because of their diverse body shapes and varying contours. Another disadvantage of the commercially available absorbent articles such as diapers, incontinent briefs and the like, is associated with the ability of opening and removing the soiled article without soiling the wearer's legs or body.

There is a plethora of patents which disclose the different attempts made by the prior art workers over the years to eliminate, or at least minimize, the shortcomings of the present commercially available absorbent articles.

For example, U.S. Pat. No. 4,909,804 issued to Herman Douglas, Jr. on Mar. 20, 1990 discloses a child toilet training pant which has a means for elasticizing the leg and waist openings by elastic bands at the waist and leg openings. The training pant described in that patent is provided with a separable side seem from the waistband to the legband on both sides in order to permit easy removal of the toddler's pant when soiled. This article does not provide for examination of the condition of the diaper and requires tearing the side seams to remove the diaper which can thus result in soiling the toddler as well as the applier.

U.S. Pat. No. 5,569,234 issued to Kenneth B. Buell et al. on Oct. 29, 1996 describes a pull-on garment provided with a continuous belt in the front region and the back region to distribute the forces generated during use in order to better fit the pull-on garment on the wearer. As in the above-mentioned patent to Douglas, Jr., the article described in Buell et al. does not provide for examination of the condition of the diaper and requires tearing a side seam for its removal, thus also causing soiling to the wearer and applier of the garment.

U.S. Pat. No. 5,607,416 issued to Masamitsu Yamamoto et al. on Mar. 4, 1997 describes a disposable absorbent pad comprising a pad member adapted to be formed into a boat shape under the contractible forces of elastic members contained in side flaps, and an elastic support member; longitudinally opposite sides of the pad member being connected to the front and rear sides of the support member by end flaps. Each of the end flaps comprises a top sheet and a back sheet and is divided in a pair of end flap halves by a slit so as to function as a suspending strap. The end flaps halves are set apart in a V-shape with the slit therebetween as the support members is stretched and contributes to suspend the pad member with high stability. The absorbent pad described in the Yamamoto et al. patent does not provide for forces to counteract the weight of the soiled pad which eventually stretches the crotch region and thus may cause leakage of urine and other body exudates through the leg openings.

U.S. Pat. No. 5,204,997 issued to Migaku Suzuki et al. on Apr. 27, 1993 describes a disposable pant-type garment, such as a diaper, which is constructed by attaching elastic surrounding flaps around the leg openings and the waist opening. This garment however is not elastically integral between the crotch and the waist portions and is not adjustable around the waist to conformably fit the body shape. Nor does this garment allow adjustment or refastening of the elastic flaps to insure body fit when the garment is soiled.

European patent application 799,002 published Jun. 6, 1996 (WO 96/19169) describes an absorbent article such as a diaper which Is provided with a closure system for anchoring the absorbent article to the wearer. The absorbent article is provided with tape tabs which are disposed at an angle of approximately 45 degree relative to the longitudinal side edges. The closure system is designed so that a plane of tension is formed at least about the front waist portion of the article to preclude rollover of the front waist portion.

European patent application 802,778 published Jul. 18, 1996 (WO 96/21412) describes a disposable diaper having an absorbent part, a pair of ear parts projecting in opposite directions from opposite side edges of one of the longitudinal end portions of the absorbent part, and two fastening means are attached to the side edges of the ear parts, respectively. Each fastening means is attached to the ear part in a pulling section of the side edge, overlapping at least part of a first side edge section and part of a second side edge section so that component tensile forces of a tensile force applied to the fastening means are distributed at a desired distribution ratio to the waist lapping portion and the leg lapping portion of the absorbent part.

European patent application 814,740 published Sep. 26, 1996 (WO 96/29038) discloses a disposable diaper having a pair of ears with oblique side edges which are inclined to extend at a predetermined angle to the longitudinal center axis of the absorbent article. The fastening means are attached to the oblique side edges and each oblique side edge has a first oblique side edge and a second oblique side edge section. Each ear has a stress relaxing structure and each fastening means is attached to the ear in order to distribute tensile forces.

The foregoing patents by no means constitute an exhaustive list of the patents which reflect the efforts of the prior art workers in this field, but are merely illustrative for background purposes. As it can be appreciated, however, notwithstanding attempts by others to provide satisfactory absorbent articles for infants as well as for incontinent adults, there is still a need for providing improved articles commercially, which are highly effective in preventing leakage of urine and other body exudates, and which are comfortable to wear and conformably fit the body contours so as to insure against such leakage and prevent soiling the wearer's body as well as the person who applies the garment to the wearer.

Accordingly, it is an object of the present invention to provide a disposable absorbent article such as baby diapers, adult incontinent underpants, briefs, guards and the like articles, which overcome the deficiencies and shortcomings of the prior art absorbent articles, including the present commercially available products used for this purpose.

It is another object of this invention to provide disposable absorbent articles which, due to their unique construction, provide improved fit to the body and prevent leakage of urine and other body exudates through the leg openings by countering the movements of the wearer and the weight of the downstretching of the crotch portion.

It is also an object of this invention to provide such disposable absorbent articles which have integral refastenable and longitudinally tensionable elastic elements which insure body fit and conformal movements in response to the body shape and contours, and provides for examination of the condition of the article.

It is a further object of the present invention to provide such disposable absorbent articles which have triple member closure system in order to insure proper distribution of the pulling forces resulting in a more perfect and snug fit of the article to the body.

The foregoing and other objects and features of the present invention will be more fully comprehended and appreciated from the ensuing detailed description and the figures in the drawing which form parts of the application.

SUMMARY OF THE INVENTION

In accordance with this invention, a disposable absorbent article is provided for use as diaper or adult incontinence brief. The article comprises an absorbent body having a front waist portion, a back waist portion, a crotch portion, a pair of spaced apart leg openings, and a fastening region intermediate the crotch portion and the front waist portion. An elasticized band member is attached to the back waist portion and has a left hand band portion and a right hand band portion, both extending angularly from the area of the back waist portion toward the fastening region. The ends of each of the band portions are adapted to be engaged to one another and to the fastening region, and they may be tensioned to securely fasten the absorbent article to the body of the wearer.

BRIEF DESCRIPTION OF THE DRAWINGS

In the drawings:

FIG. 3A is a sectional view taken along the line 3A—3A of FIG. 3;

DETAILED DESCRIPTION OF THE INVENTION

Figure 1:
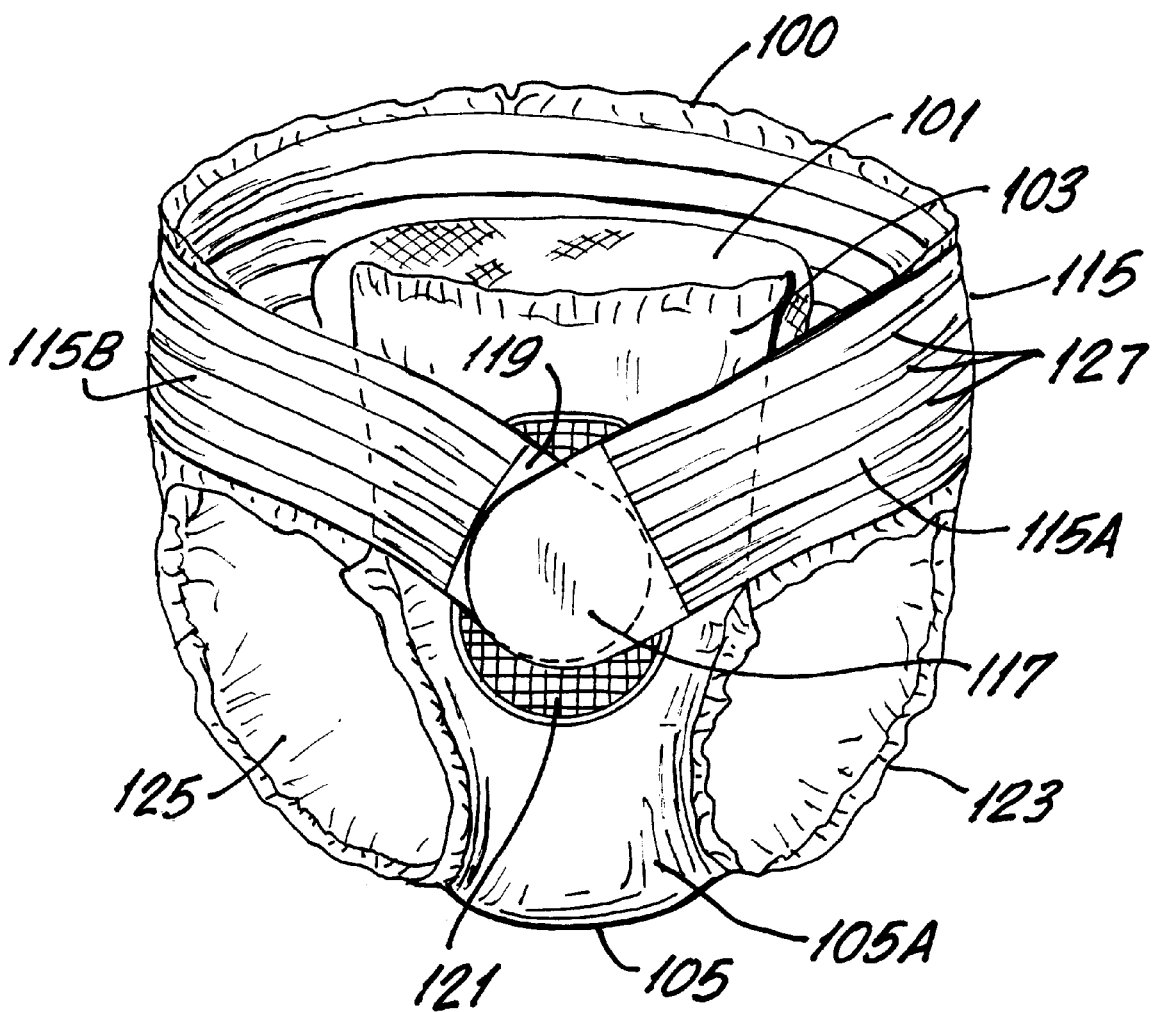
FIG. 1 is a perspective view of a pant-type absorbent article made in accordance with one embodiment of the present invention having elastic band (belt) and a triple member closure in the front waist region, in fastened position.

Referring first to FIG. 1 of the drawings, there is shown an absorbent article in the form of a brief, generally designated as 100. The term "brief" as used herein is intended to refer to disposable garments worn below the lower part of the torso by incontinent persons and also comprises disposable articles such as baby diapers, adult incontinent underpants, guards and the like articles. The absorbent article 100 comprises a back waist region 101, a front waist region 103 and a crotch region 105 having a front crotch portion 105A. Referring to FIG. 3A, the absorbent article 100 comprises a liquid pervious top sheet or layer 107 facing the body of the wearer, a liquid impervious backsheet 109 which is usually coextensive with the top layer 107, and an absorbent layer or pad 111 disposed between the top sheet 107 and backsheet 109. An acquisition layer 113 is disposed between the top sheet 107 and the absorbent layer 111 and serves to temporarily retain the body exudates and slowly distribute them through the absorbent pad 111. These layers are sealed at their corresponding ends to form a composite sheet.

Figure 12:
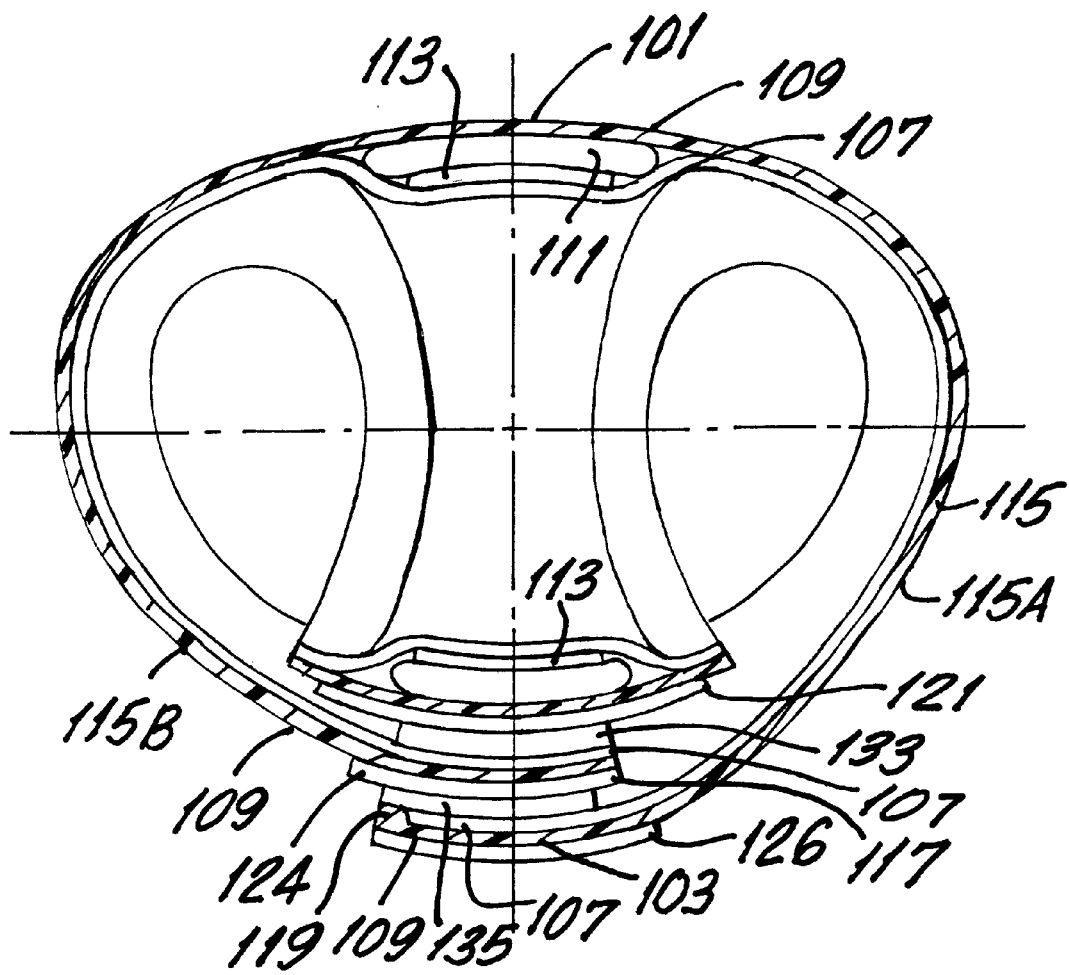
FIG. 12 is a cross sectional view taken along the line 12—12 of FIG. 2, in fastened position, illustrating the different layers of the absorbent pad and the triple member closure region.
Figure 13:
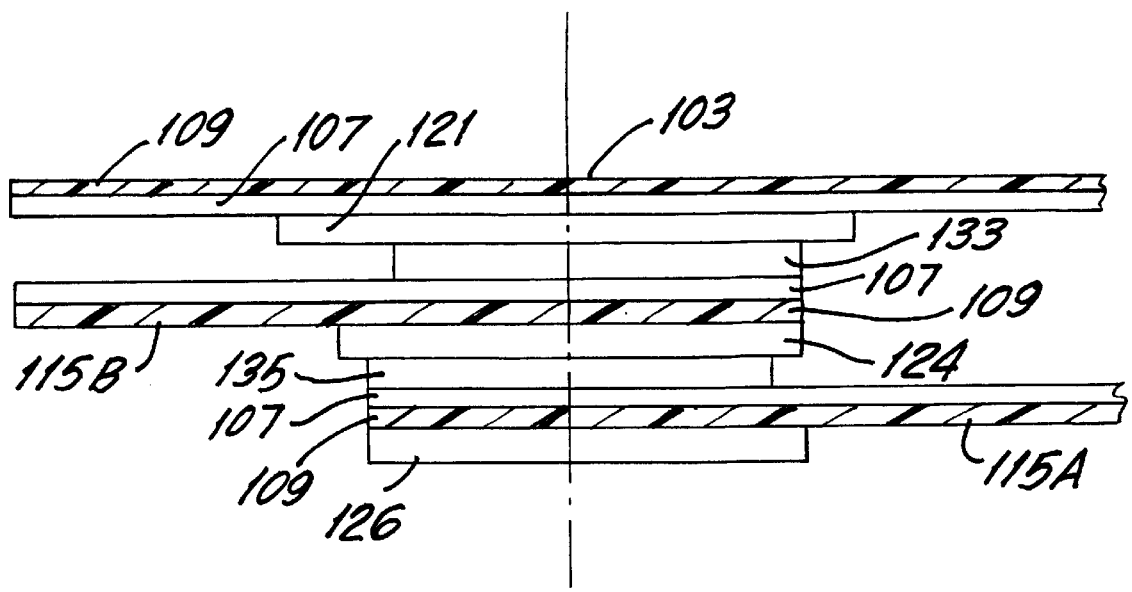
FIG. 13 is an enlarged view of portion of the triple closure member region, in fastened position.
Figure 14:
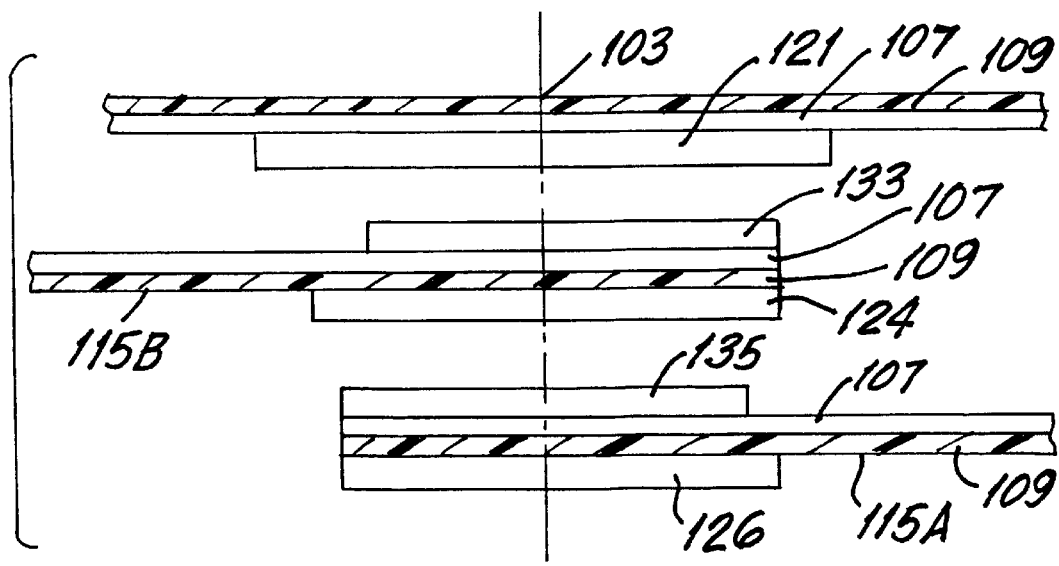
FIG. 14 is an enlarged view similar to FIG. 13 but wherein the triple member closure is shown in unfastened position.

The absorbent article 100 shown in FIG. 1 has an elastic band or belt 115 which is attached to the back waist portion 101 and extends around the waist angularly toward the crotch region as a left hand belt portion 115A and right hand belt portion 115B. As shown in FIGS. 12, 13 and 14 the left hand belt portion 115A terminates in a fastenable closure end 117 and the right hand belt portion 115B terminates in the fastenable closure end 119. These ends are adapted to be engaged to one another and to the fastening region 121 in the front of the article thereby providing a triple member closure defined by inter-engagement of the respective ends 117,119 of the belt portions 115A–115B, and the fastening region 121. Thus, each end portion (117,119) has an inner adherent surface 133,135 and an outer non-adherent surface 124,126. The fastening region 121 is also a non-adherent surface, therefore, in fastened position the inner adhering surface of one end is securely adhered to the outer non-adhering surface of the other end, and the inner adhering surface of the other end is securely adhered to the non-adhering surface of the fastening region to form a triple member closure as shown in FIGS. 12, 13 and 14. There is also shown in FIG. 12 (fastened position) the liquid pervious backsheet 107 and the liquid impervious layer 109 and the absorbent layer 111 interposed therebetween.

The absorbent article 100 also comprises the leg openings 123,125, and the belt portions 115A, 115B each comprises elastic elements 127 which impart elasticity to the article. Alternatively, the elastic belt 115 itself may be made of an elastic material in which case the elastic elements 127 are not required. Both belt portions 115A,115B of the elastic belt 115 are disposed angularly toward the crotch region 105 as is further illustrated in FIGS. 2, 3, 4–10. FIG. 4 shows the angular disposition of the elastic band or belt relative to the horizontal axis of the article. This angle, may vary depending on the body shape and the location of the fastening region 121, which itself may constitute a large or small area as desired.

Figure 5:
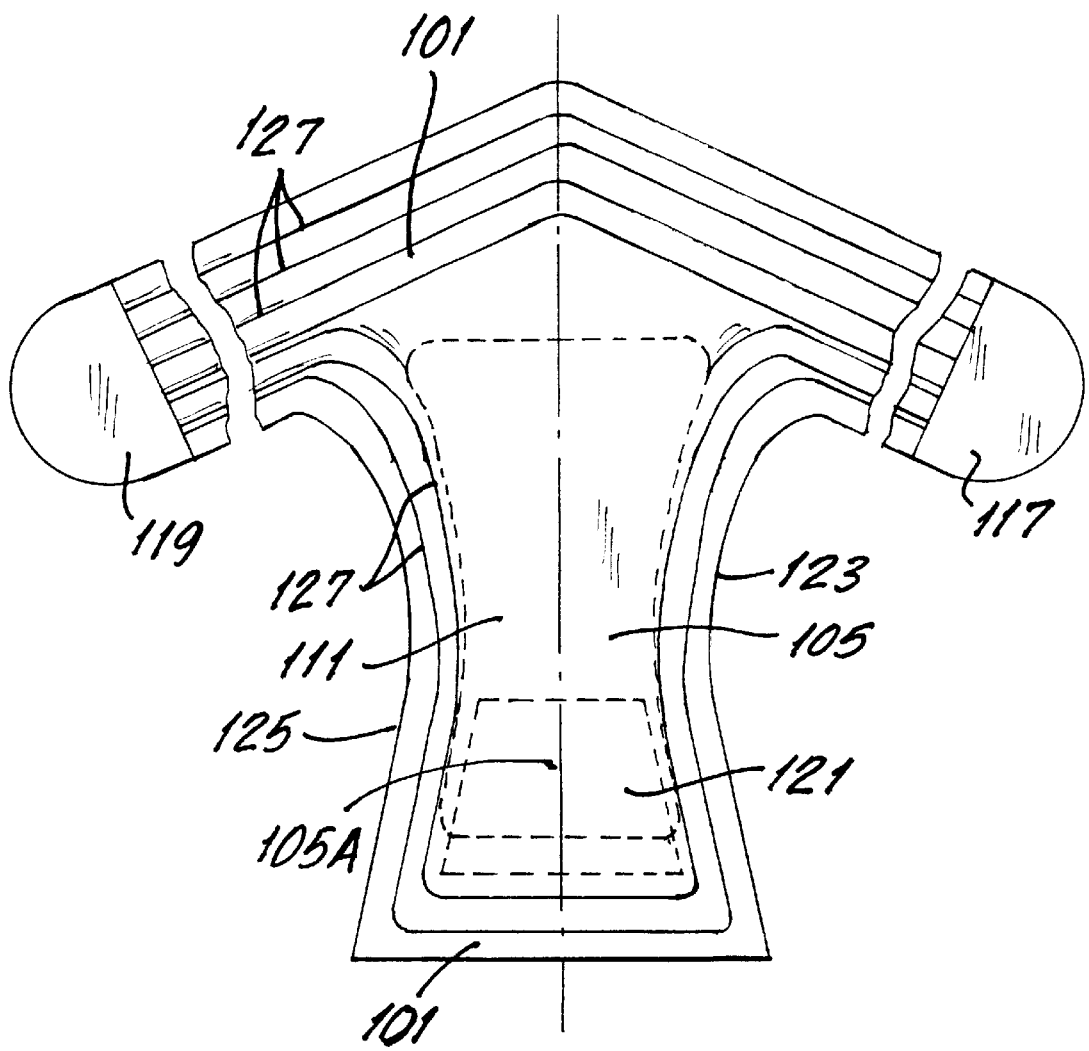
FIG. 5 is a stretched plan view of the absorbent article similar to FIG. 3 but wherein the ends of the elastic band are angularly disposed from the center of the back waist portion toward the front of the crotch portion.
Figure 6:
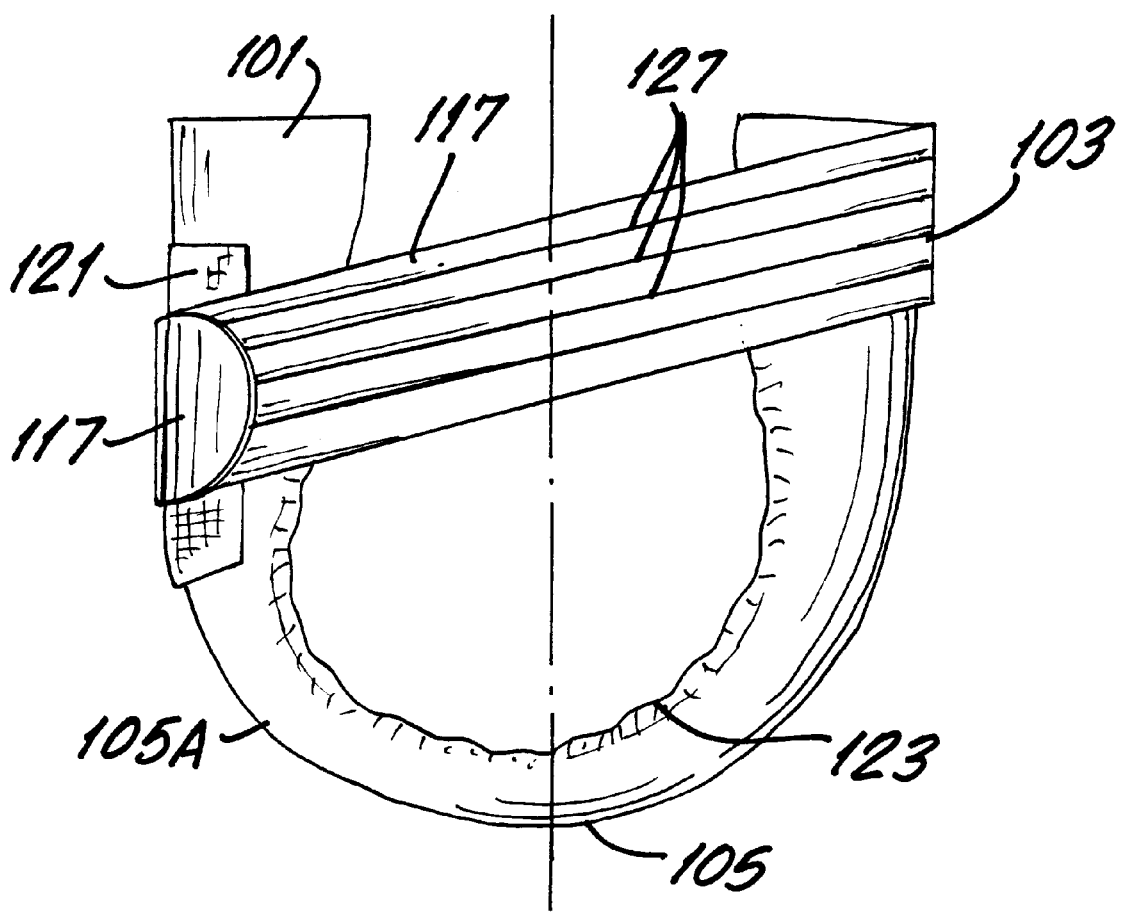
FIG. 6 is a plan view of the left view of the absorbent article shown in FIG. 1.
Figure 7:
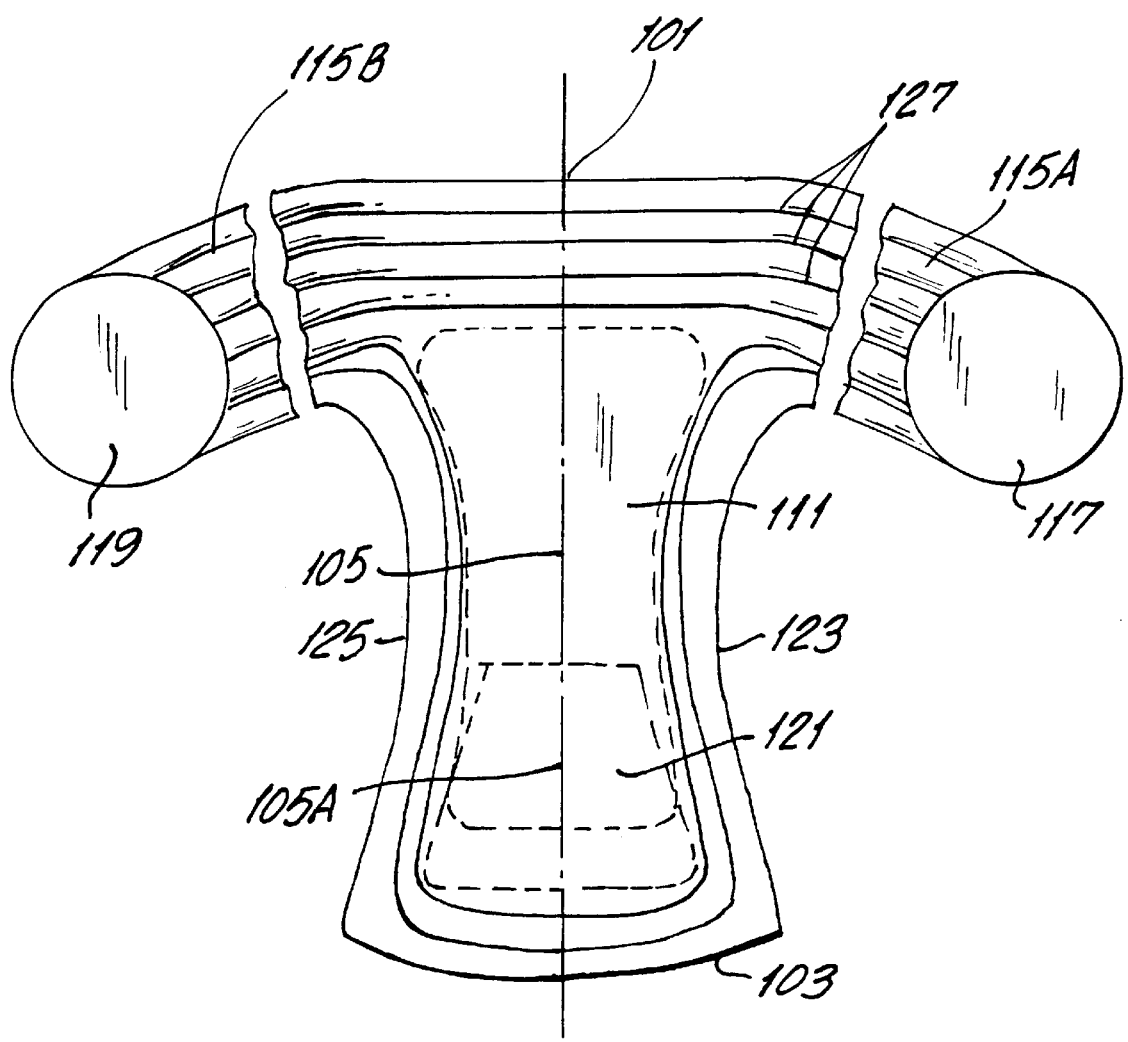
FIG. 7 is another stretched plan view similar to FIG. 3 but wherein the ends of the elastic band are angularly disposed curvilinearly from the hip toward the front crotch portion.
Figure 8:
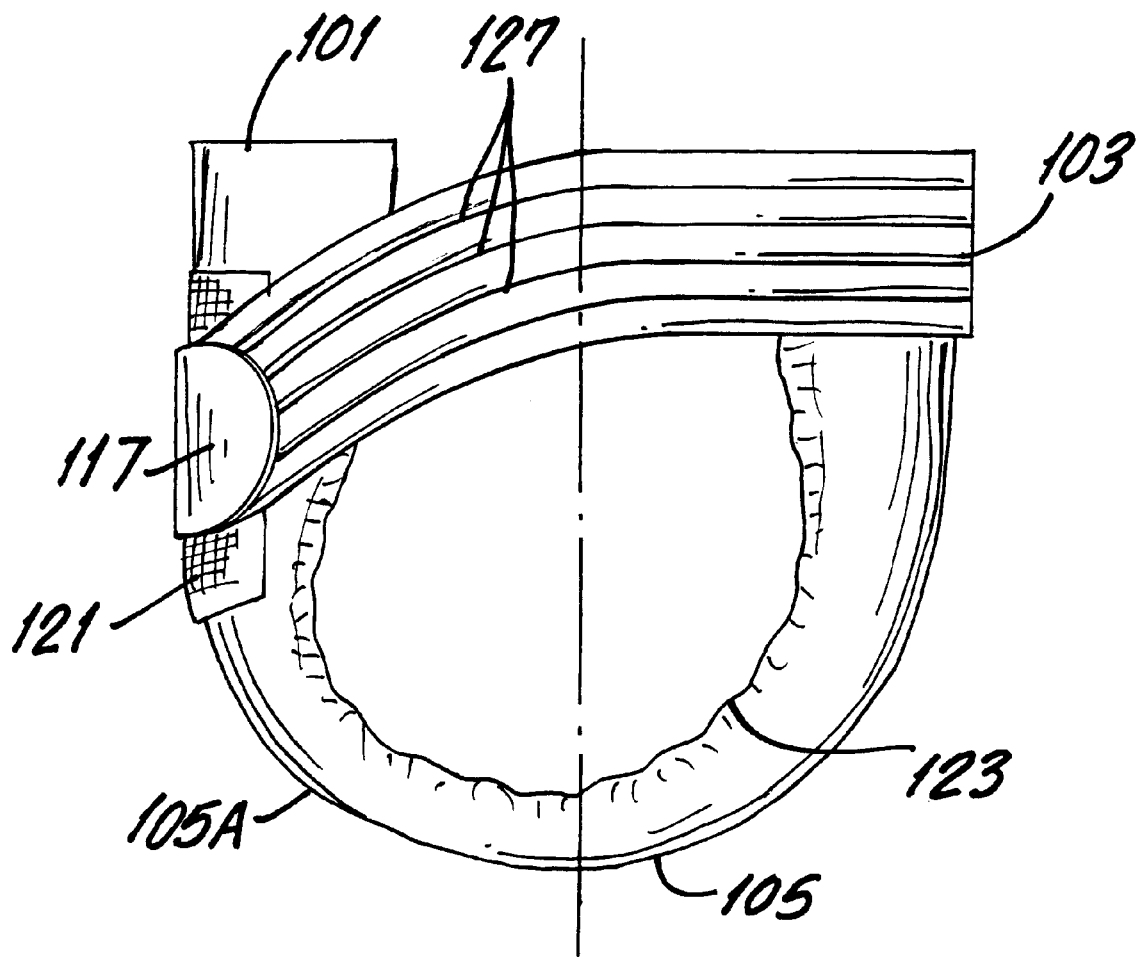
FIG. 8 is a plan view of the left side of the absorbent article in FIG. 1 with the ends of the elastic band disposed curvilinearly as in FIG. 7.
Figure 9:
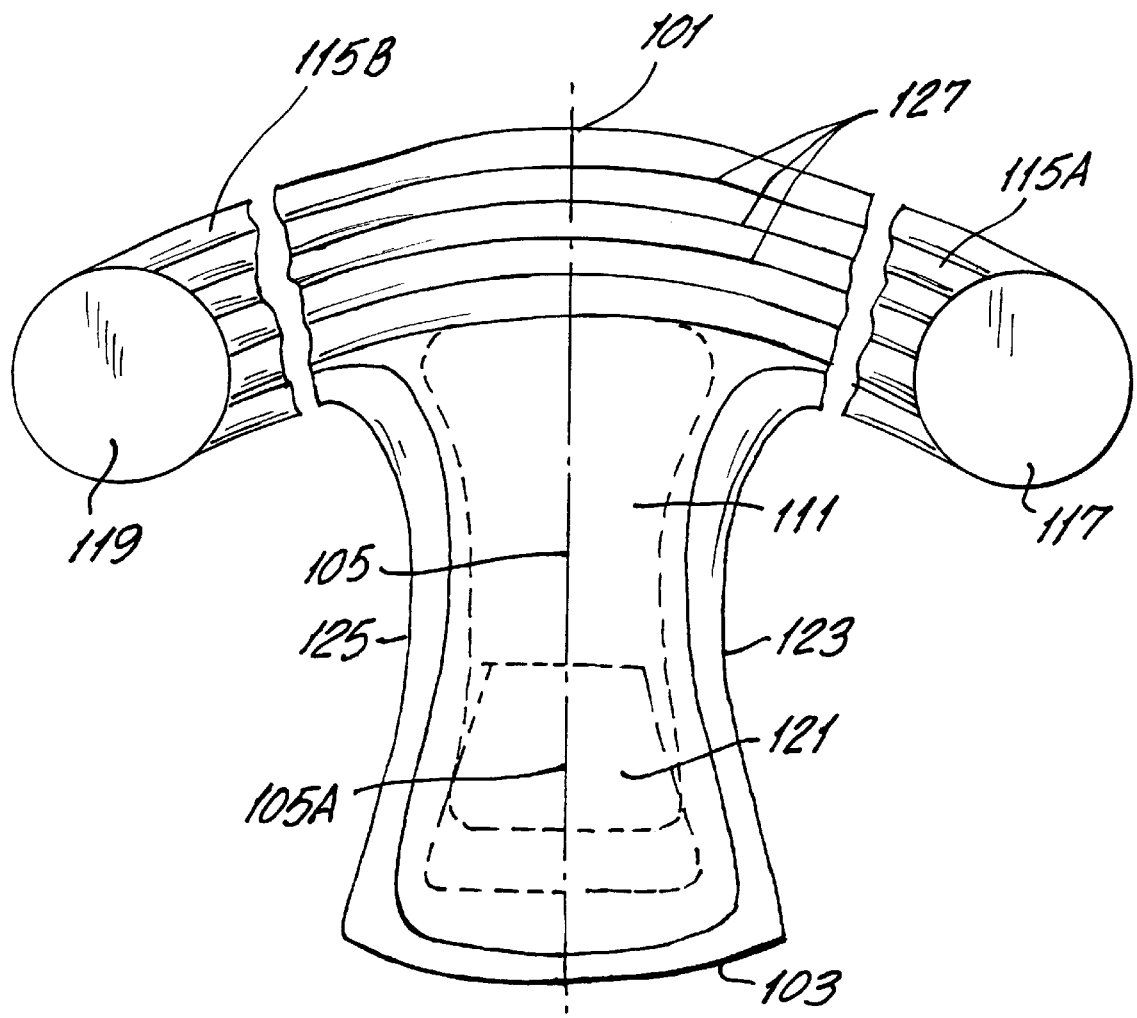
FIG. 9 is a stretched plan view similar to FIG. 7 but wherein the ends of the elastic band are angularly disposed curvilinearly from the center of the back waist portion toward the front of the crotch portion.
Figure 10:
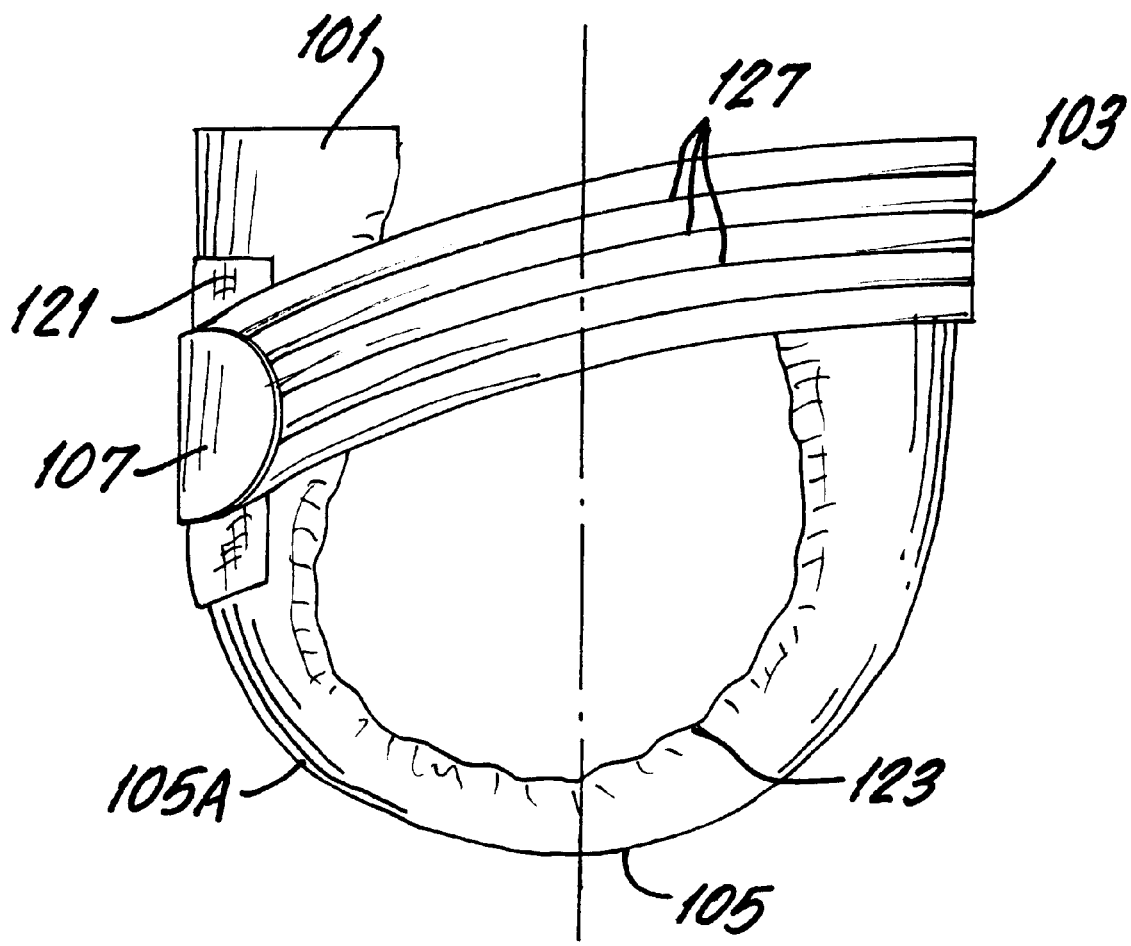
FIG. 10 is a plan view of the left side of the absorbent article shown in FIG. 1 with the ends of the elastic bands disposed curvilinearly as shown in FIG. 9.

In FIG. 5, the elastic belt 115, and hence the elastic elements 127 of the belt, are angularly disposed from the center of the back waist portion of the article toward the front crotch region. This construction is further illustrated in FIG. 6.

In FIGS. 1–6, the elastic elements 127 of the elastic belt 115, and its respective band portions 115A, 115B are shown extending linearly, i.e., in relatively straight substantially parallel lines angularly toward the crotch region. In FIGS. 7–10, the elastic elements are shown to extend curvilinearly, at an angle relative to the horizontal axis of the article. Thus, in FIGS. 7 and 8 the elastic elements 127 extend curvilinearly, at an angle, from the hip toward the front of the crotch region, and in FIGS. 9 and 10 the elastic elements 127 are disposed angularly curvilinearly from the center of the back waist portion toward the front of the crotch region.

While reference is made to linear or curvilinear elastic belt, it should be mentioned that these refer to the fabricated, pre-use appearance of the elastic belt since in use, and as a practical matter, the elastic belt conforms to the contours of the body of the wearer.

Also, while the elastic belt portions 115A,115B are shown extending angularly from the hip to the front crotch region (see FIGS. 3, 4, 7 and 8), these elastic belt portions may, in a different variation, extend from the center of the back waist portions to the front crotch region (see FIGS. 5, 6, 9 and 10), or the elastic belt may extend from any point between the center of the back waist and the hip toward the crotch region. All these structures and configurations are within the scope of the present invention.

Figure 1A:
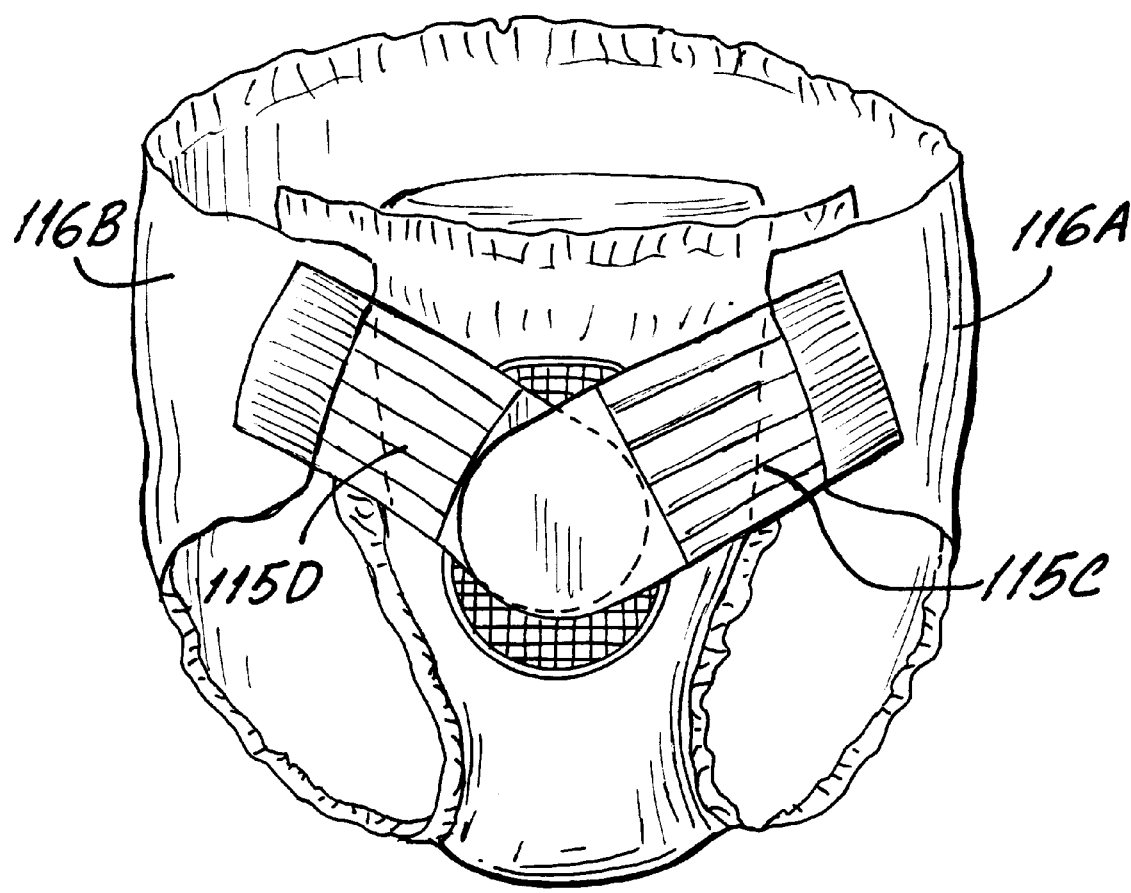
FIG. 1A is similar to FIG. 1 except that two separate elastic band members are used to form the triple member closure.
Figure 2:
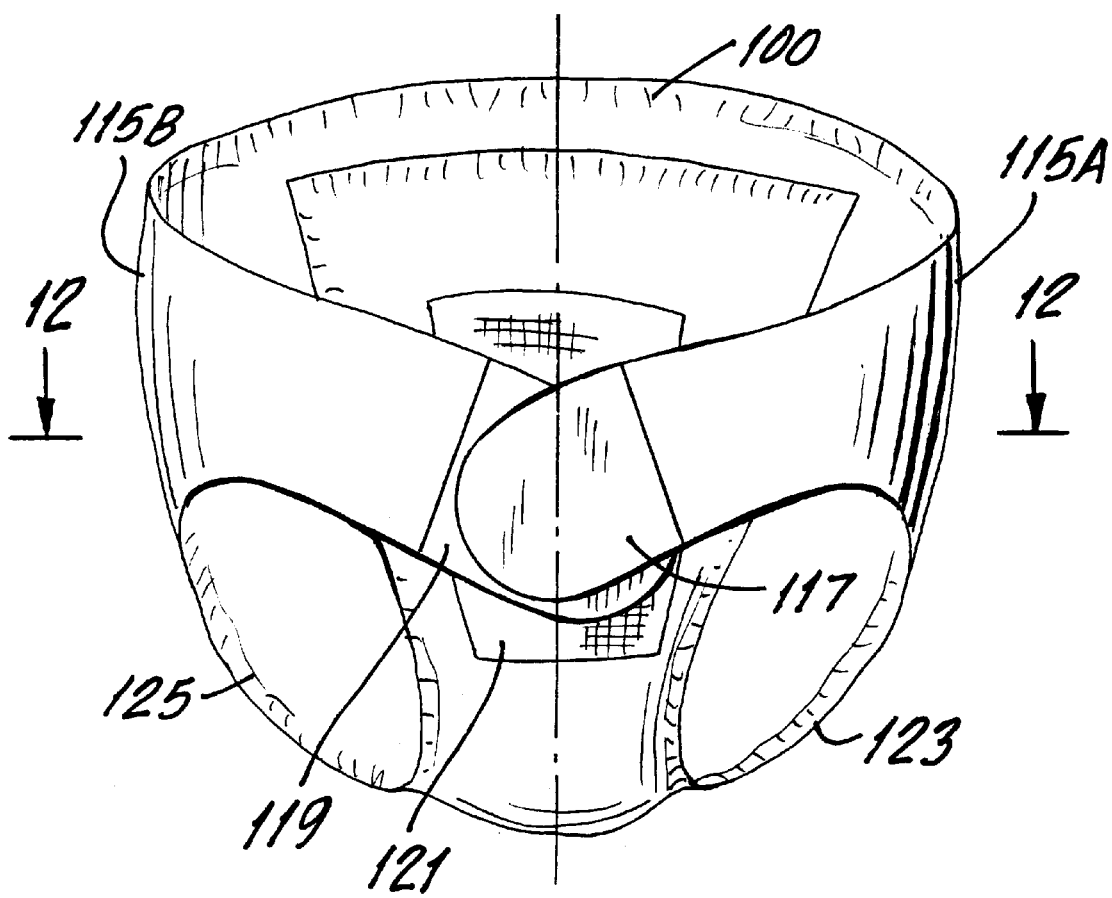
FIG. 2 is a plan view of the front of the absorbent article shown in FIG. 1.

As shown in FIG. 1A, the elastic band need not be a continuous band but rather, one could use two separate elastic band members 115C,115D which may be secured to the left and right hips at 116A,116B respectively. Otherwise, the structure of the absorbent article is the same as in FIG. 1.

Figure 3:
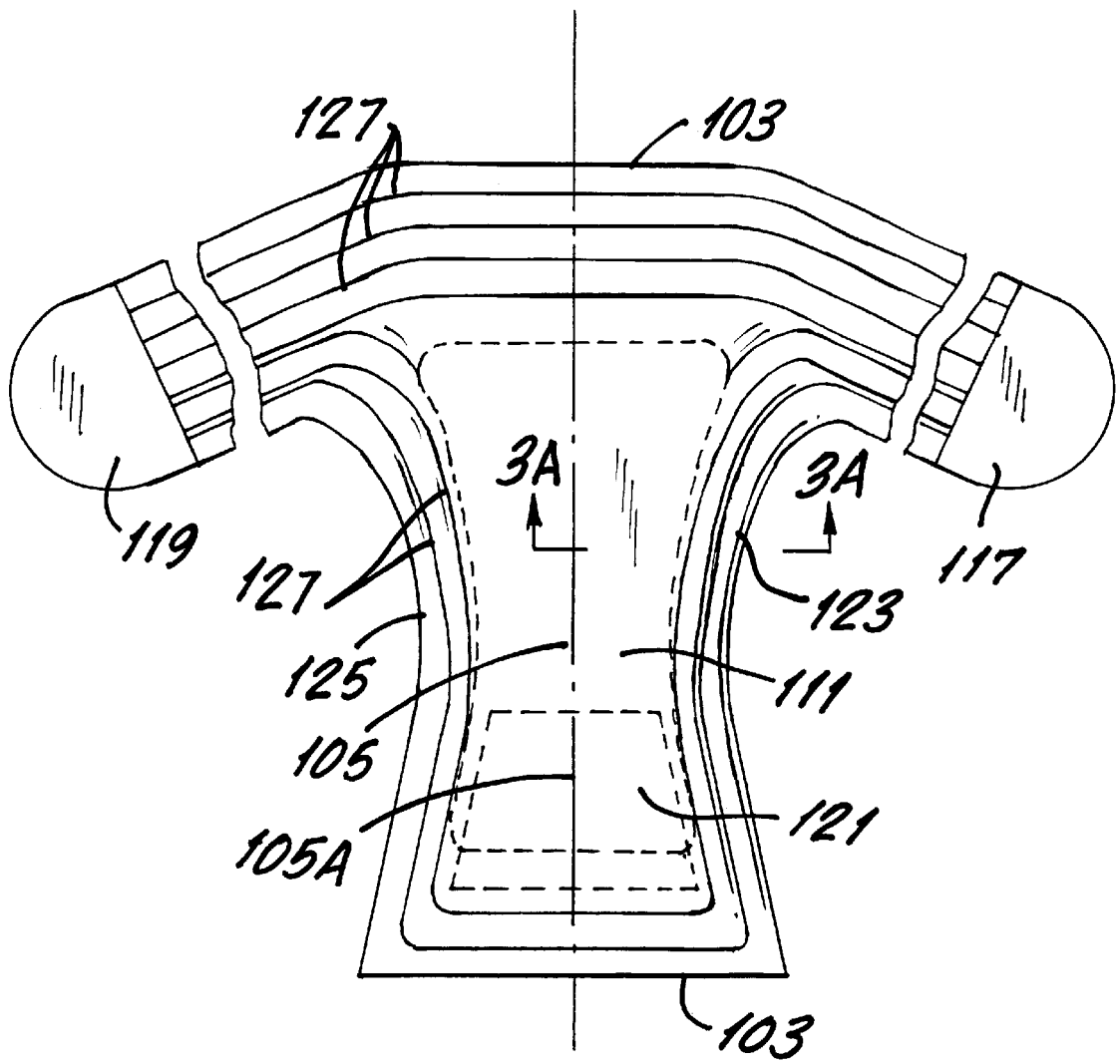
FIG. 3 is a stretched plan view of the absorbent article in FIG. 1 showing the elastic band angularly disposed at both ends, from the hip toward the front crotch portion.
Figure 4:
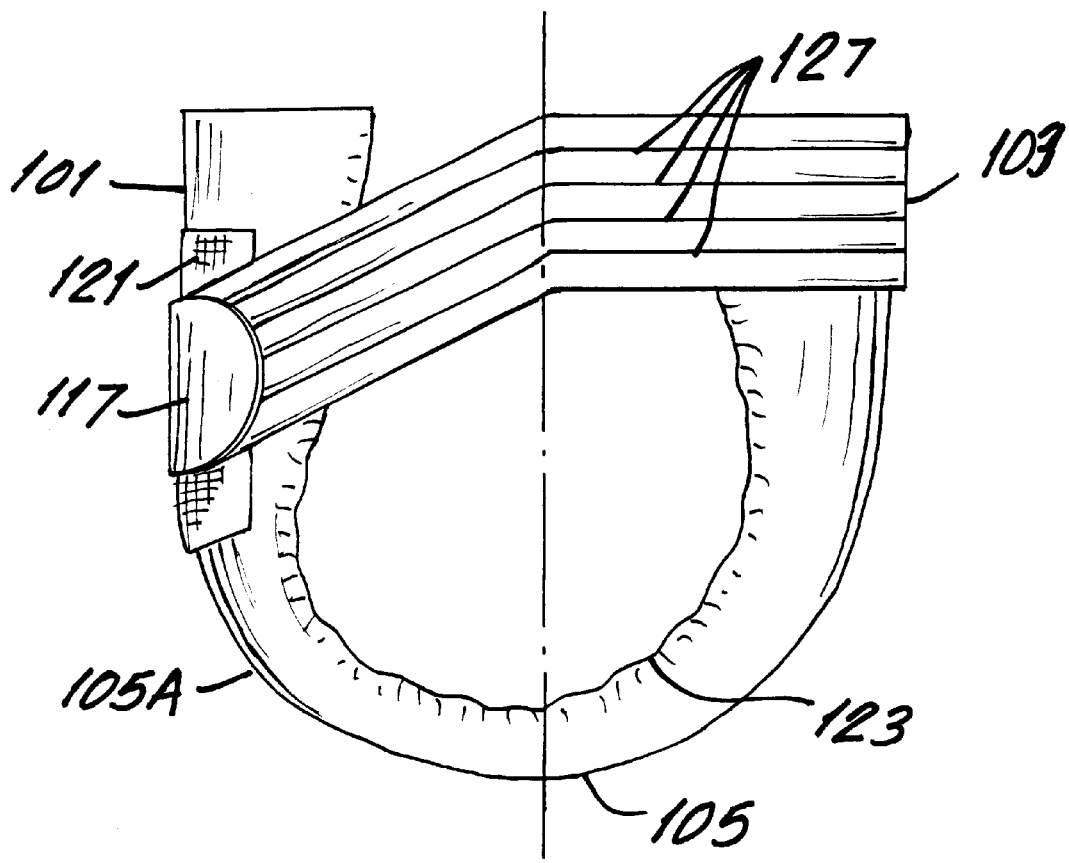
FIG. 4 is a plan view of the left side of the absorbent article shown in FIG. 1.
Figure 11:
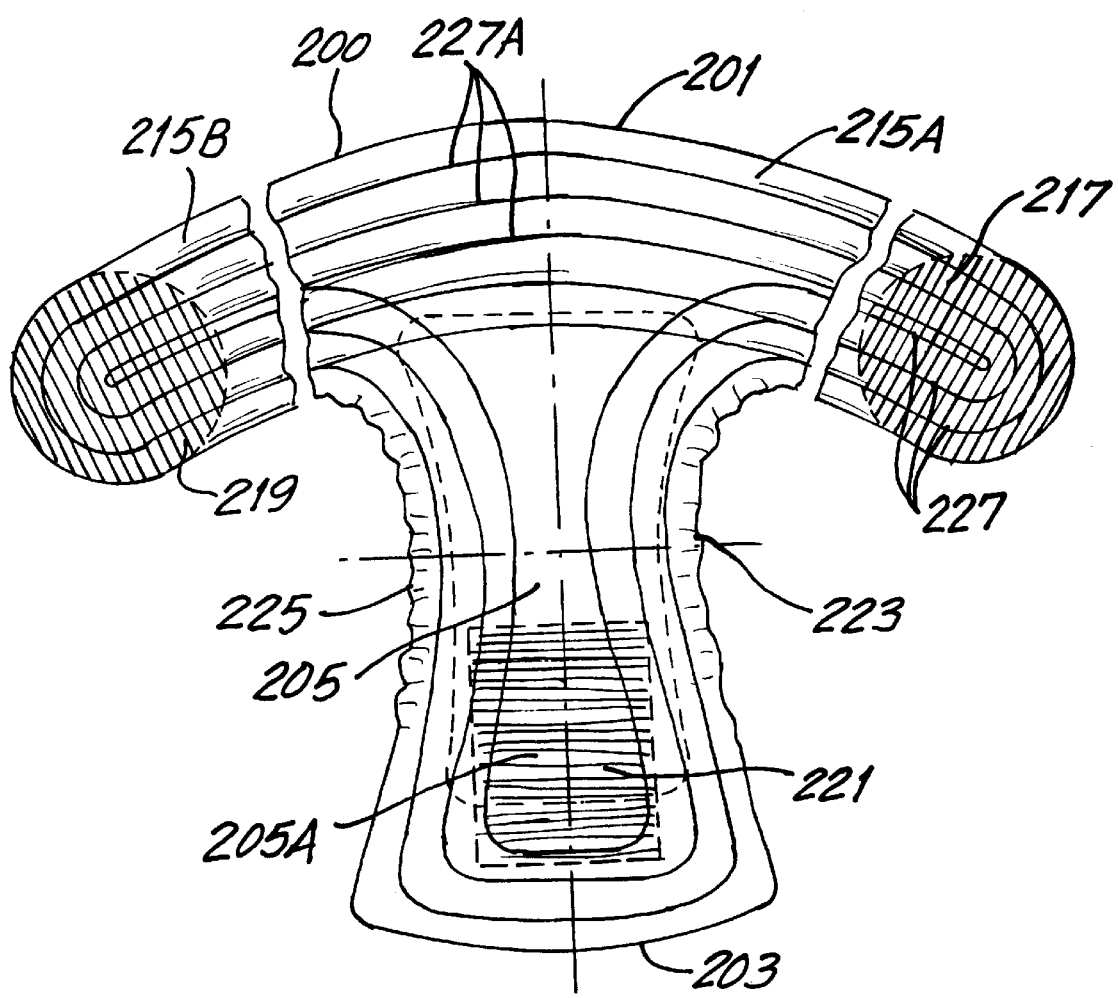
FIG. 11 is stretched plan view of an absorbent article similar to FIG. 9 but wherein the elastic elements are formed into respective loops attached to the elastic band.

Referring to FIG. 11, the absorbent article 200 shown therein is similar in structure to the absorbent article 100 shown in FIG. 3 except that the elastic elements are formed into respective loops 227A. Also as in the absorbent article shown in FIGS. 1–3, the absorbent article 200 has an elastic band or belt 215 which extends around the waist as in the previous embodiment, i.e., into a left hand belt portion 215A and a right hand belt portion 215B. However, the elastic elements 227 of the elastic belt 215 are formed into loops which span from the end 217 to the end 219 of the respective belt portions 215A and 215B. At its front, the absorbent article 200 has a fastening region 221, and the leg openings 223 and 225. As in the previous embodiments, each of the ends of the belt portions 215A and 215B has an outer non-adherent surface and an inner adherent surface for fastening and unfastening of the ends of the belts relative to each other and to the fastening region 221 which has an outer non-adherent surface.

It must be noted that the layered structure depicted in FIGS. 13 and 14 is the same for all embodiments of the invention and are numbered uniformly for the sake of consistency.

Figure 15:
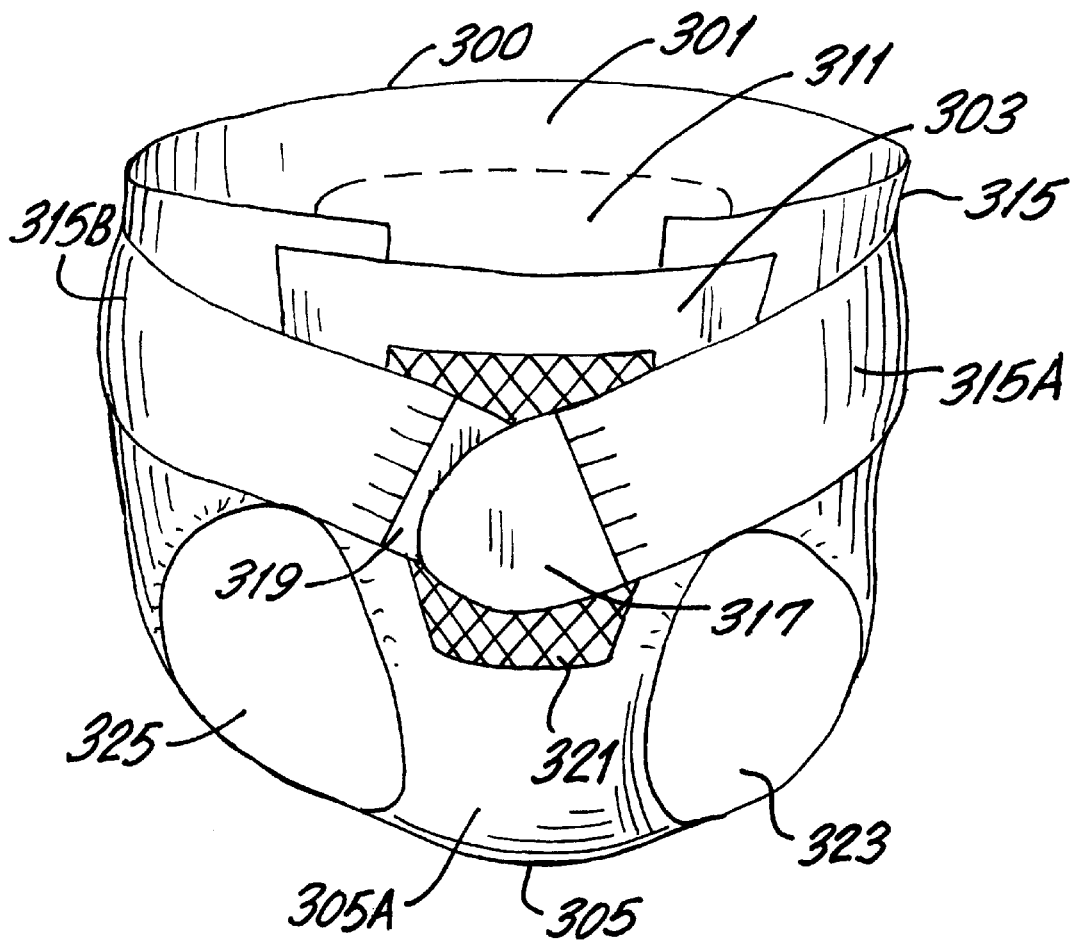
FIG. 15 is a perspective view of a different embodiment of an absorbent article having a triple member closure similar to the absorbent article shown in FIG. 1 but wherein a separate elastic band is attached to the center of the back waist portion of the article.
Figure 16:
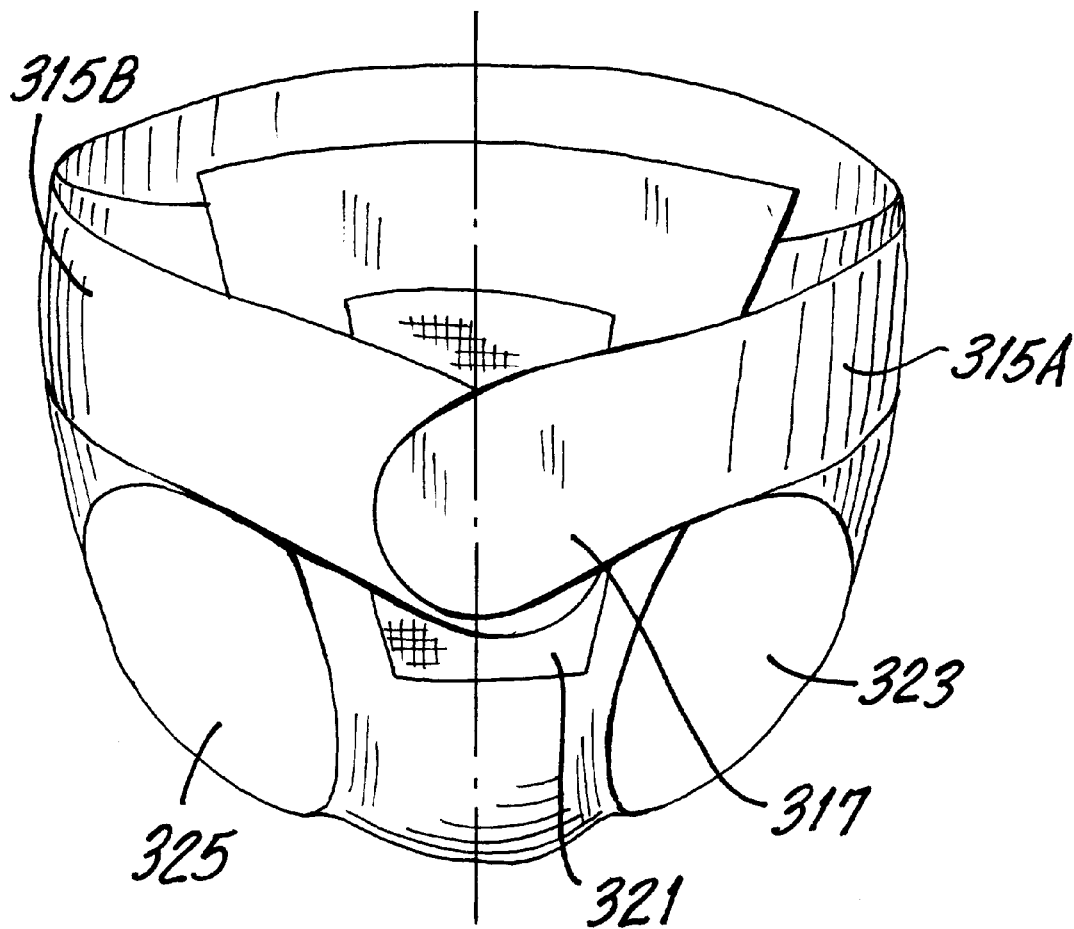
FIG. 16 is a plan view of the front of the absorbent article shown in FIG. 15 with the separate elastic bands in fastened position.

In FIGS. 15 and 16, the absorbent article 300 has a back waist portion 301 and a front waist portion 303, and is provided with a separate elastic band 315 attached to the backwaist portion 301. As in the previously described embodiments the elastic belt 315 comprises the left hand elastic belt portion 315A and the right hand elastic belt portion 315B having their respective ends 317 and 319 attached to the fastening region 321. As in the previous embodiments the absorbent article 300 comprises the absorbent panel 311, the leg openings 323 and 325 and the crotch region 305 having a front crotch region 305A.

Figure 17:
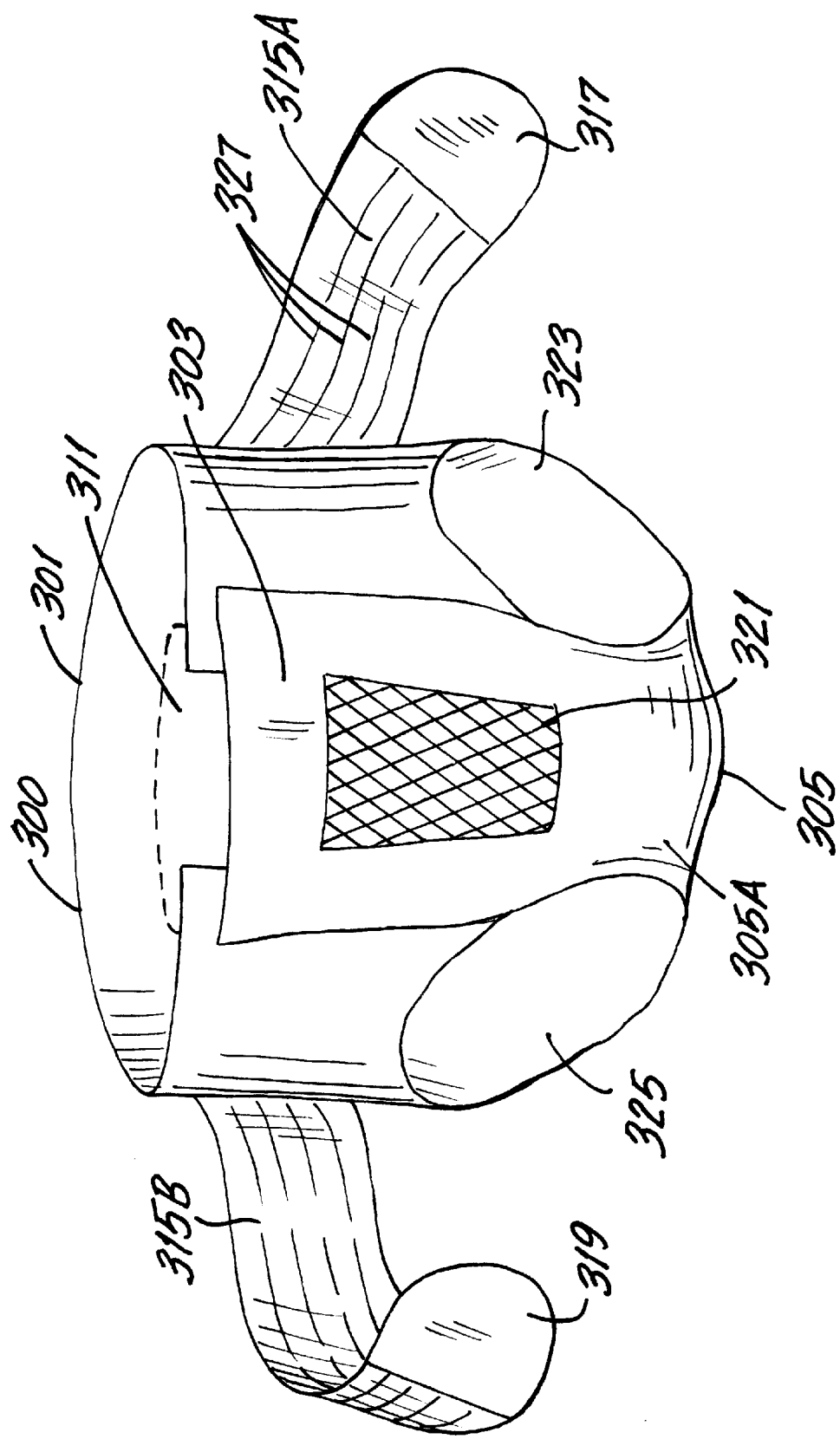
FIG. 17 is a perspective view of the absorbent article shown in FIG. 15 but wherein the separately attached elastic band is in open (unfastened) position.
Figure 18:
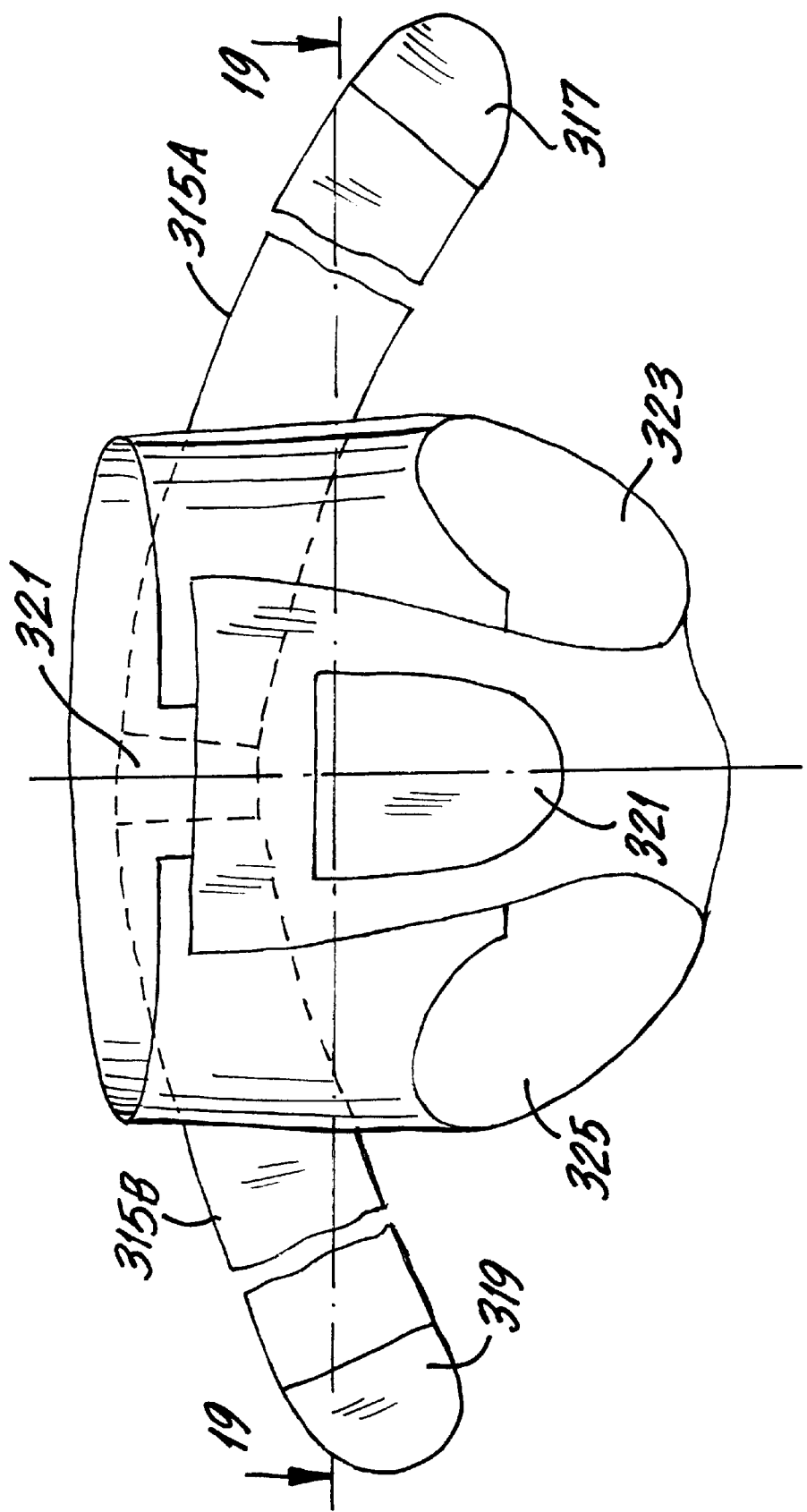
FIG. 18 is a plan view of the front of the absorbent article shown in FIG. 17.

FIGS. 17 and 18, similar to FIGS. 15 and 16, respectively, except that the ends of the elastic belt are in unfastened position. Thus, as shown in FIG. 17, the absorbent article 300 comprises a back waist portion 301, a front waist portion 303 having a left hand front waist portion 303A a right hand front waist 303B, a crotch region 305, a front crotch region 305A, a fastening region 321 and leg openings 323,325.

Figure 19:
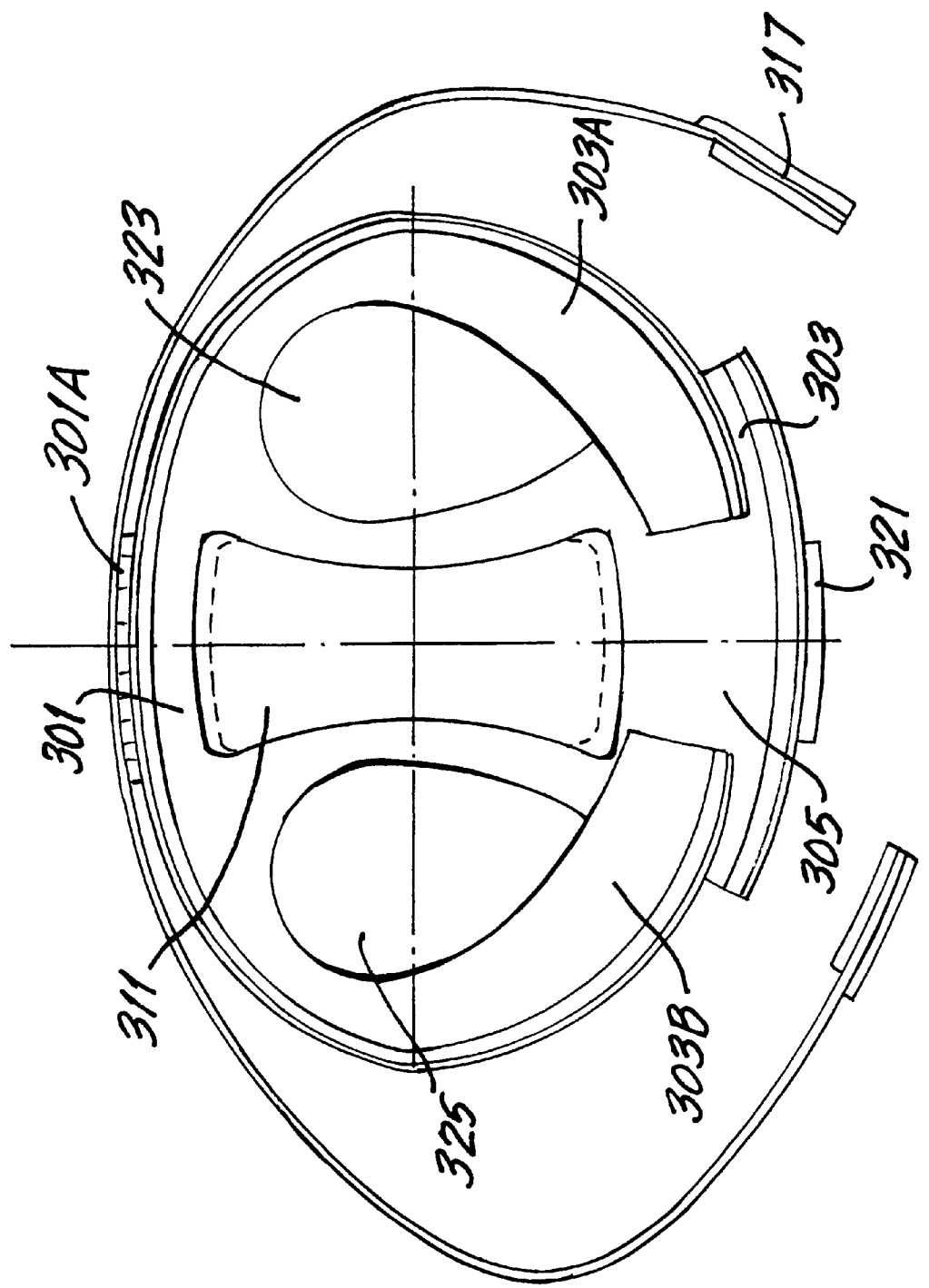
FIG. 19 is a cross sectional view taken along the line 19—19 of FIG. 18.
Figure 20:
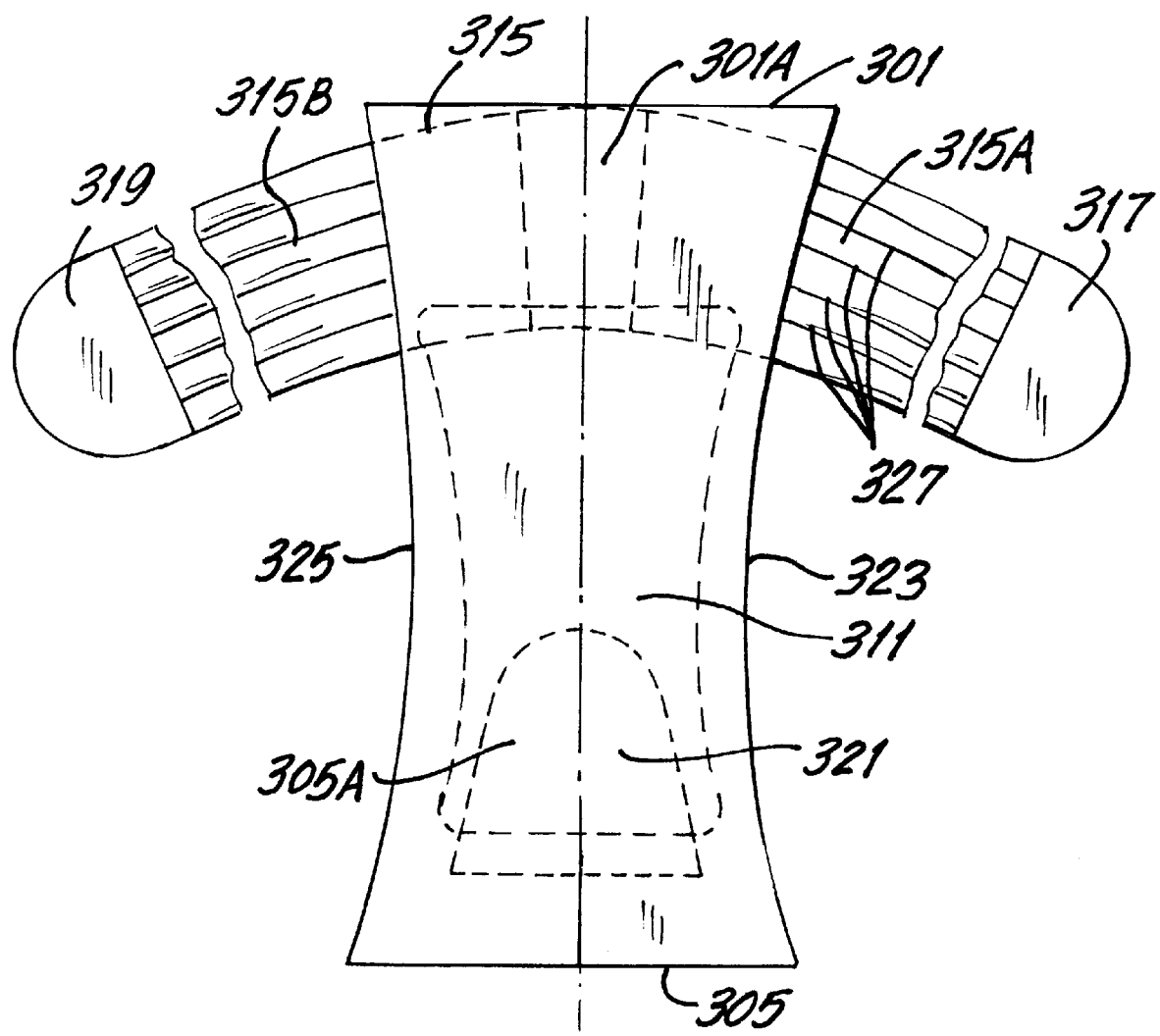
FIG. 20 is a stretched plan view of the absorbent article shown in FIG. 17.

FIGS. 19 and 20 show more clearly how the separate elastic belt 315 is attached to the back waist attachment region 301A of the backwaist portion 301 of the absorbent article and extends as the left and right elastic belts portions 315A,315B angularly disposed toward the fastening region 321. As in the previous embodiments, the ends 317,319 of the elastic belt portions 315A,315B are adapted to adherently overlap on one another and on the fastening region 321 to form a triple member closure. In the embodiment shown in FIG. 19, the left hand belt portion 317 overlaps the right hand portion 319, however the overlapping positions of the ends 317,319 may be reversed. Alternatively, the ends of the belts may be simply tied together if desired.

Figure 21:
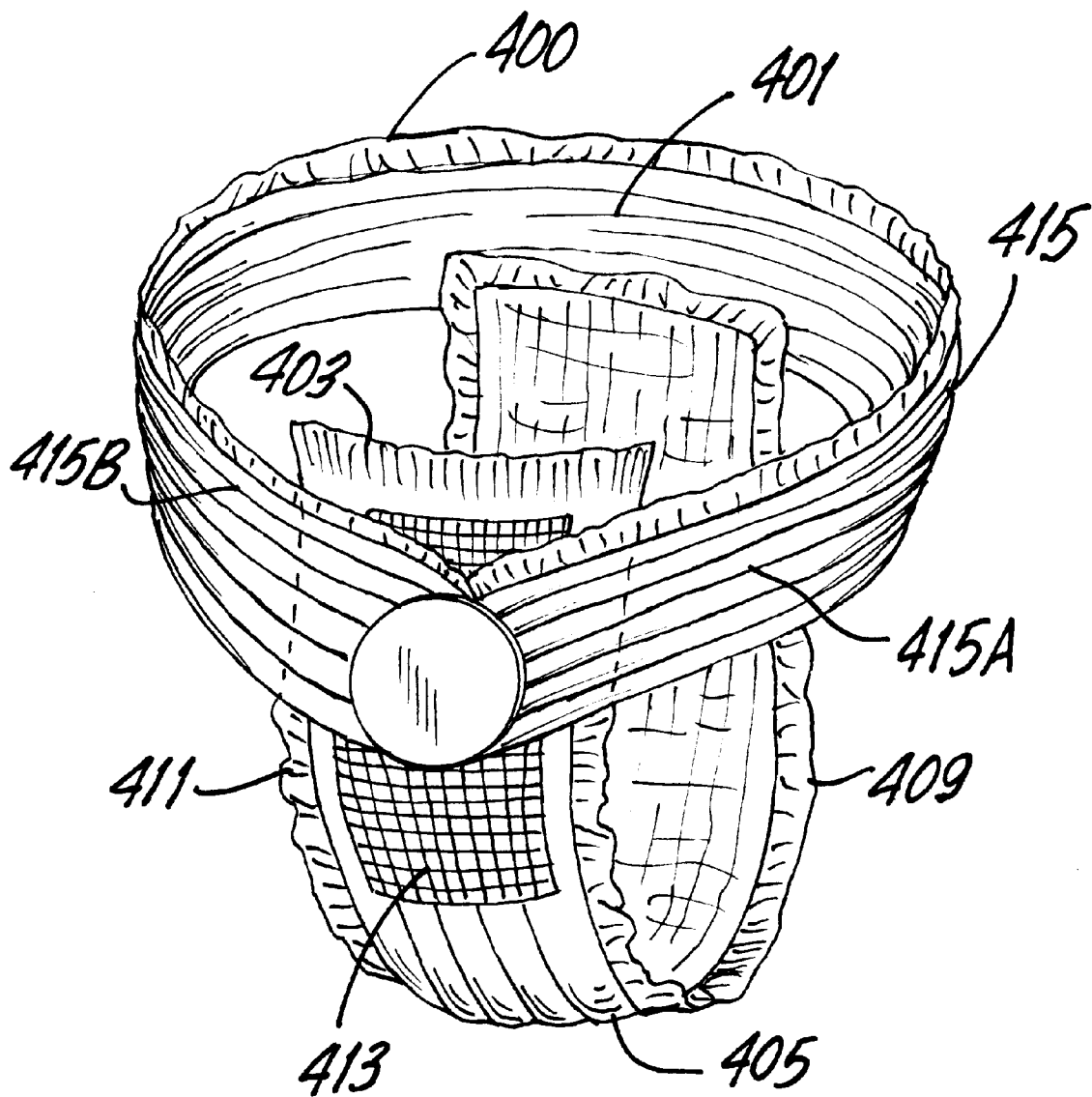
FIG. 21 is a perspective view of an absorbent article made according to another embodiment of this invention having triple member closure fastened in the front portion, and separate elastic band attached to the rear portion of the absorbent pad of the article.
Figure 22:
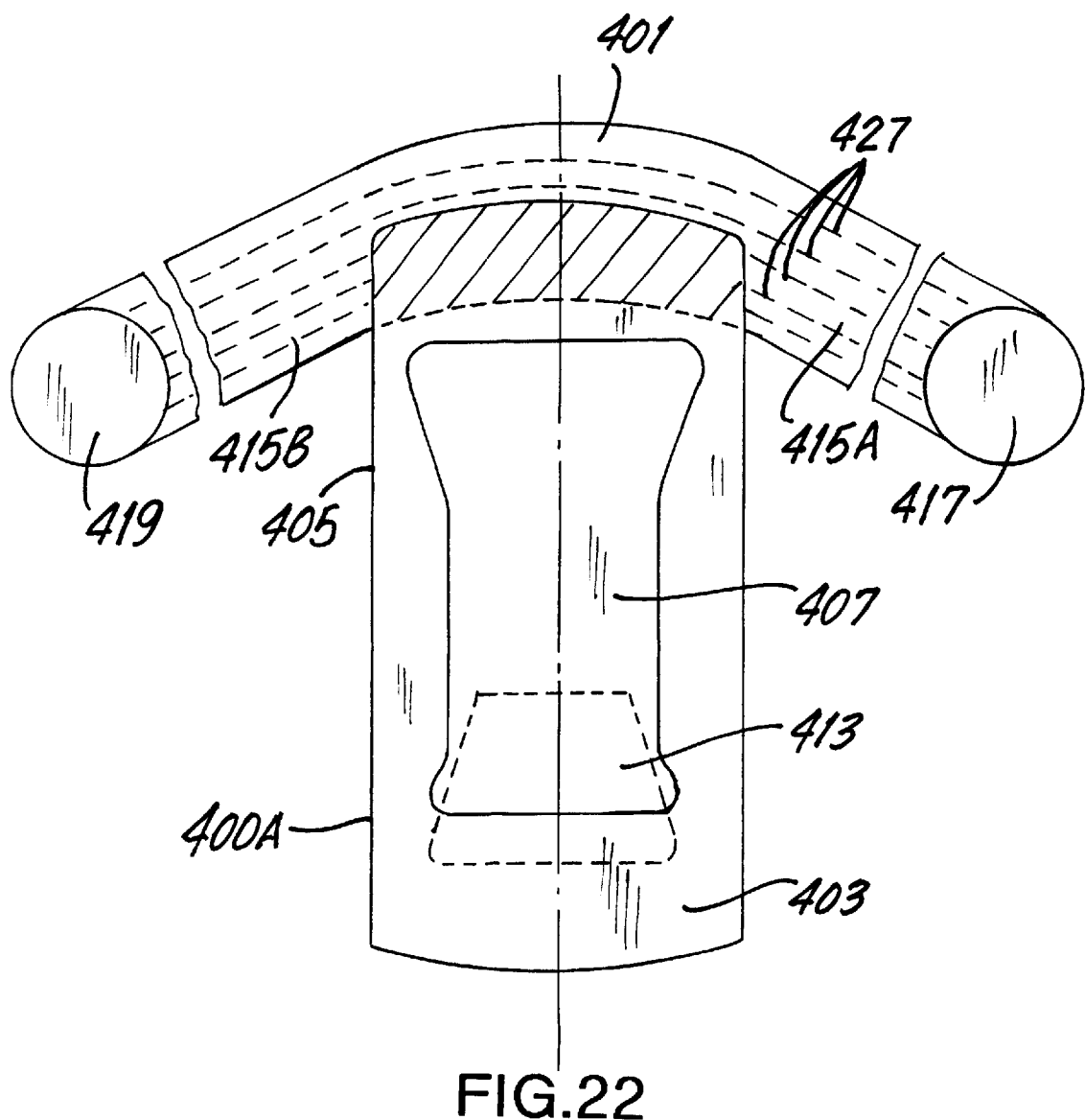
FIG. 22 is a stretched plan view of the absorbent article shown in FIG. 21 but wherein the separate elastic band is in an open (unfastened) position.

In FIGS. 21 and 22, the absorbent article 400 is a two piece construction basically consisting of a separate elastic belt and absorbent body portion. The body portion 400A comprises a back waist portion 401, a front waist portion 403, a crotch region 405, a front crotch region 405A, an absorbent layer or pad 407, the leg openings 409 and 411 and a front waist fastening region 413. The absorbent article shown in FIGS. 21 and 22 also has a separate elastic band or belt 415 which is attachable at the back waist portion 401 around the waist portion and extends angularly toward the crotch region as a left hand belt portion 415A and a right hand belt portion 415B. The left hand belt portion 415A terminates in the end 417 and the right hand belt portion 415B terminates in the end 419. As in the previously described embodiments, the ends 417 and 419 are adapted to engage to one another and to the front waist fastening region 413 to form a triple member closure.

In all embodiments of the present invention, rather than using adherent and non-adherent surfaces to secure the ends of the belts and the fastening regions, these surfaces may be provided with so-called "hook-and-loop" arrangement, male-female members or any other suitable mechanical means.

The materials of construction of the different layers of the absorbent article described in each embodiment of the invention are described in copending application Ser. No. 09/097,198 filed Jun. 12, 1998 in the name of Mordechai Turi, the disclosure of which is fully incorporated herein by reference. Referring to FIG. 3A, the absorbent article comprises the top sheet or layer 107, the backsheet 109, the absorbent layer 111 and the acquisition layer 113. The top sheet 107 and the backsheet 109 are adhesively secured together by the construction adhesive A and the elastic elements 127 are adhesively secured to the top sheet 107 and the backsheet 109 by means of the elastic adhesive B.

In the preferred practice of the present invention, the elastic belts and the elastic elements are available as System 7000 from the Fulflex Company, Middletown, R.I. and the hot melt adhesive is available from H. B. Fuller Company, St. Paul, Minn. as Code No. HL-1434-X-ZP.

The materials and fabrics used in the construction of the absorbent article of the invention are of the type and variety known in the art and are described in several patents such as, for example, U.S. Pat. Nos. 4,695,278 and 4,795,454.

Thus, the liquid pervious top layer 107 is a compliant soft material which is not irritating to the skin. Such material can be made from porous foams, reticulated foams, plastics, natural fibers, such as wood or cotton fibers, synthetic fibers such as polyester or polypropylene fibers, or made from a combination of said materials. A suitable polypropylene material is available from First Quality Fibers, Inc., McElhattan, Pa., as grade 15 ILWH.

The liquid impervious backsheet or layer 109 is preferably manufactured from a thin flexible plastic film such as polyethylene film available from Clopay Plastic Products Company, Cincinnati, Ohio, as grade DH-203.

The absorbent layer 111 may be manufactured from a wide variety of liquid absorbent materials of the type usually used in manufacturing disposable diapers and other absorbent articles. Such materials include comminuted wood pulp, creped cellulose wadding, absorbent foams, absorbent sponges, super absorbent polymers or a combination of said materials.

The acquisition layer 113 is made from a nonwoven material which temporarily retain the exudates and distributes them in the absorbent layer. Such material is available from American Nonwoven Corporation, Columbus, Miss., as grade RB-265-14-B/R.

The construction adhesives employed in the present invention is a hot melt adhesive available from Reynolds, Inc., Greensville, S.C. as Reynolds Code No. 51-942.

In use, the disposable absorbent article of the present invention is placed around the waist with the waistband tensioned and pulled toward the fastening region so that the absorbent article fit snugly but comfortably to the shape of the wearer's body, while the legs extend through the leg openings. The tensioned belts are then secured by securing their respective ends together and to the fastening region.

While the present invention has been described and illustrated with reference to several embodiments with certain degree of specificity, other embodiments and modifications are obvious to those skilled in the art based on the detailed description herein without departing from the scope of the invention.

What is claimed is:

1. An integral disposable elasticized absorbent article comprising:
    (a) an absorbent body having a front waist portion, a back waist portion, a crotch portion and a paid of spaced apart leg openings;
    (b) a fastening region intermediate said crotch portion and said front waist portion, said fastening region having an outer surface and,
    (c) an elasticized band member attached to said back waist portion, said elasticized band member having a left hand band portion and a right hand band portion, each of said band portions extending angularly toward said fastening region, each of said band portions having an end portion, wherein each of said end portions has in inner surface and an outer surface and wherein, in fastened position, the inner surface of one end portion is secured to the outer surface of the other end portion, and the inner surface of said other end portion is secured to the surface of said fastening region.

2. An integral disposable elasticized absorbent article comprising:
   (a) an absorbent body having a front waist portion, a back waist portion, a crotch portion and a pair of spaced apart leg openings,
   (b) a fastening region intermediate said crotch portion and said front waist portion, said fastening region having an outer surface,
   (c) a liquid pervious top layer facing the body of the wearer,
   (d) a liquid impervious back layer substantially coextensive with said liquid pervious layer,
   (e) a liquid absorbent layer disposed between said liquid pervious top layer and liquid impervious back layer, said liquid absorbent layer being substantially coextensive with said liquid pervious layer and said liquid impervious back layer and being sealed to said layers, and
   (f) an elasticized band member attached to said back waist portion, said elasticized band member having a left hand band portion and a right hand band portion, each of said band portions extending angularly toward said fastening region, each of said band portions having an end portions, wherein each of said end portions has an inner surface and an outer surface and wherein, in fastened position, the inner surface of one end portion is secured to the outer surface of the other end portion, and the inner surface of said other end portion is secured to the surface of said fastening region.

3. An integral disposable elasticized absorbent article as in claim 1 wherein said elasticized band member comprises at least one elasticized band element formed into a loop extending from one end of the elasticized band member to the other end of the elasticized band member.

4. An integral disposable elasticized absorbent article as in claim 2 wherein said elasticized band member comprises at least one elasticized band element formed into a loop extending from one end of the elasticized band member to the other end of the elasticized band member.

5. A disposable elasticized absorbent article comprising:
   (a) an absorbent body having a front waist portion, a back waist portion, a crotch and a pair of spaced apart leg openings;
   (b) a fastening region intermediate said crotch portion and said front waist portion, said fastening region having an outer surface, and
   (c) a separate elasticized band member attached to said back waist portion said elasticized band member having a left hand band portion and a right hand band portion, each of said band portions extending angularly toward said fastening region, each of said band portions having an end portion, wherein each of said end portions has an inner surface and an outer surface and wherein, in fastened position, the inner surface of one end portion is secured to the outer surface of the other end portions, and the inner surface of said other end portion is secured to the non-adherent surface of said fastening region.

6. A disposable elasticized absorbent article comprising:
   (a) an absorbent body having a front waist portion, back waist portion a crotch portion and a pair of spaced apart leg openings;
   (b) a fastening region intermediate said crotch portion and said front waist portion of said absorbent article, said fastening region having an outer surface,
   (c) a liquid pervious top layer facing the body of the wearer;
   (d) a liquid impervious back layer substantially coextensive with said liquid pervious layer;
   (e) a liquid absorbent layer disposed between said liquid pervious top layer and liquid impervious back layer, said liquid absorbent layer being substantially coextensive with said liquid pervious top layer impervious layer and being sealed to said layers, and
   (f) a separate elasticized band member attached to said back waist portion, said elasticized band member having a left hand band portion and a right hand band portion, each of said band portions extending angularly toward said fastening region, each of said band portions having an end portion, wherein each of said end portions has an inner surface and an outer surface and wherein, in fastened position, the inner surface and an outer surface and wherein, in fastened position, the inner surface of one end portion is secured to the outer surface of the other end portion, and the inner surface of said other end portion is secured to the surface of said fastening region.

7. A disposable elasticized absorbent article as in claim 5 wherein said elasticized band member comprises at least one elasticized band element formed into a loop extending from one end of the elasticized band member to the other end of the elasticized band member.

8. A disposable elasticized absorbent article as in claim 6 wherein said elasticized band member comprises at least one elasticized band element formed into a loop extending from one end of the elasticized band member to the other end of the elasticized band member.

9. A two-piece disposable elasticized absorbent article comprising, as a first separate piece, an absorbent body having a front waist portion, a back waist portion, a crotch portion, a pair of spaced apart leg openings, and a fastening region intermediate said crotch portion and said back waist portion, said fastening region having an outer surface and,
   in combination therewith, as a second separate piece, an elasticized band member attachable to said back waist portion, said elasticized band member having a left hand band portion and a right hand band portion, each of said band portions extending angularly toward said fastening region, each of said band portions having an end portion, wherein each of said end portions has an adherent surface and an outer surface and wherein, in fastened position, the inner surface of one end portion is secured to the outer surface of the other end portion, and the inner surface of said other end portion is secured to the surface of said fastening region.

10. A two-piece disposable absorbent article comprising, as a first separate piece, an absorbent body having a front waist portion, a back waist portion, a crotch portion, a pair of spaced apart leg openings, and a fastening region intermediate said crotch portion and said front waist portion of said absorbent article, said fastening region having an outer surface, a liquid pervious top layer facing the body of the wearer, a liquid impervious back layer substantially coextensive with said liquid pervious top layer and liquid impervious absorbent layer disposed between said liquid pervious top layer an liquid impervious back layer, said liquid absorbent layer being substantially coextensive with said liquid pervious top layer and said liquid impervious back layer and being sealed to said layers, in combination therewith, as a second separate piece, an elasticized band member attachable to said back waist portion, said elasticized band member having a left hand band portion and a right hand band portion, each of said band portions extending from the back waist portion angularly toward said fastening region, and each of said band portions having an end portion, wherein each of said end portions has an inner surface and an outer surface and wherein, in fastened position, the inner surface of one end portion is secured to the outer surface of the other end portion, and the inner surface of said other end portion is secured to the surface of said fastening region.

11. A two-piece disposable absorbent article as in claim 10 wherein said elasticized band member comprises at least one elaticized band element formed into a loop extending from one end of the elasticized band member to the other end of the elasticized band member.

12. A two-piece disposable absorbent article as in claim 10 wherein said elasticized band member comprises at least one elasticized band element formed into a loop extending from one end of the elasticized band member to the other end of the elasticized band member.

13. An integral disposable elasticized absorbent article comprising:

(a) an absorbent body having a front waist portion, a back waist portion, a crotch portion and a pair of spaced apart leg openings, said absorbent article being adapted for wearing around the hip portion of the wearer, (b) a fastening region intermediate said crotch portion and said front waist portion, said fastening region having an outer surface and, (c) a left hand band member and a right hand band member, each of said band members extending angularly from its respective hip portion toward said fastening region, each of said band members having an end portion, wherein each of said end portions has an inner surface and an outer surface and wherein, in fastened position, the inner surface of one end portion is secured to the outer surface of the other end portion, and the inner surface of said other end portion is secured to the surface of said fastening region.

14. An integral disposable elasticized absorbent article comprising:

(a) an absorbent body having a front waist portion, a back waist portion, a crotch portion and a pair of spaced apart leg openings, said absorbent article being adapted for wearing around the hip portion of the wearer, (b) a fastening region intermediate said crotch portion and said front waist portion of said absorbent article, said fastening region having an outer surface and, (c) a liquid pervious top layer facing the body of the wearer;

(d) a liquid impervious back layer substantially coextensive with said liquid pervious layer;

(e) a liquid absorbent layer disposed between said liquid pervious top layer and liquid impervious back layer, said liquid absorbent layer being substantially coextensive with said liquid pervious top layer and said liquid impervious back layer and being sealed to said layers, and (f) a left hand band member and a right hand band member, each of said band members extending angularly from its respective hip portion toward said fastening region, each of said band portions having an end portion, wherein each of said end portions has an inner surface and an outer surface and wherein, in fastened position, the inner surface of one end portion is secured to the outer surface of the other end portion, and the inner surface of other end portion is secured to the surface of said fastening region.

* * * * *